US007947726B2

(12) United States Patent
Scanlan et al.

(10) Patent No.: US 7,947,726 B2
(45) Date of Patent: *May 24, 2011

(54) NON-STEROIDAL LIGANDS FOR THE GLUCOCORTICOID RECEPTOR, AND COMPOSITIONS THEREOF

(75) Inventors: Thomas S. Scanlan, Portland, OR (US); Nilesh Shah, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/365,106

(22) Filed: Feb. 3, 2009

(65) Prior Publication Data

US 2009/0137655 A1 May 28, 2009

Related U.S. Application Data

(60) Continuation of application No. 10/972,250, filed on Oct. 22, 2004, now Pat. No. 7,485,660, which is a division of application No. 10/350,260, filed on Jan. 22, 2003, now Pat. No. 6,831,093.

(60) Provisional application No. 60/351,484, filed on Jan. 22, 2002, provisional application No. 60/373,757, filed on Apr. 17, 2002.

(51) Int. Cl.
*A61K 31/416* (2006.01)
*C07D 231/54* (2006.01)
(52) U.S. Cl. .................. 514/406; 548/356.1; 548/358.1; 548/359.1; 514/410; 514/411
(58) Field of Classification Search ............... 548/356.1, 548/358.1, 359.1, 427; 514/406, 410, 411
See application file for complete search history.

(56) References Cited

U.S. PATENT DOCUMENTS

| | | | |
|---|---|---|---|
| 3,135,743 | A | 6/1964 | Clinton et al. |
| 6,139,873 | A | 10/2000 | Hughes, Jr. et al. |
| 6,451,834 | B1 | 9/2002 | Arnold et al. |
| 6,462,036 | B1 | 10/2002 | Doyle et al. |
| 6,518,294 | B2 | 2/2003 | Teng et al. |
| 6,831,093 | B2 | 12/2004 | Scanlan et al. |
| 7,026,484 | B2 | 4/2006 | Zhi et al. |
| 7,071,333 | B2 | 7/2006 | Combs et al. |
| 7,109,196 | B2 | 9/2006 | Wang et al. |
| 7,122,570 | B2 | 10/2006 | Koppitz et al. |
| 7,132,533 | B2 | 11/2006 | Benedict et al. |
| 7,485,660 | B2 | 2/2009 | Scanlan et al. |
| 7,645,885 | B2 * | 1/2010 | Scanlan et al. ............. 548/359.1 |
| 2006/0074120 | A1 | 4/2006 | Ali et al. |

FOREIGN PATENT DOCUMENTS

| | | |
|---|---|---|
| CA | 1178965 | 4/1984 |
| CA | 1167040 | 8/1984 |
| DE | 1169442 | 5/1964 |
| EP | 0102404 | 3/1984 |
| EP | 1467730 | 10/2004 |
| GB | 934574 | 8/1963 |
| GB | 1071124 | 6/1967 |
| WO | WO 99/33786 | 7/1999 |
| WO | WO 99/41257 | 8/1999 |
| WO | WO 00/06137 | 2/2000 |
| WO | WO 00/07972 | 2/2000 |
| WO | WO 03/086294 | 10/2003 |
| WO | WO 2004/066920 | 8/2004 |
| WO | WO 2004/093805 | 11/2004 |
| WO | WO 2006/124710 | 11/2006 |

OTHER PUBLICATIONS

International Search Report, dated Jun. 6, 2003, issued in International Application No. PCT/US03/01997.
Coghlan, M.J., Elmore, S.W. et al., "Chapter 17: Selective Glucocorticoid Receptor Modulators", *Annual Reports in Medicinal Chemistry*, vol. 37, 2002.
Medical Encyclopedia: Prostate Cancer [online], [retrieved on Sep. 24, 2007], 5 pages. Retrieved from the Internet: <URL: http://www.nlm.nih.gov/medlineplus/ency/article/000380.htm>.
Medical Encyclopedia: Androgen insensitivity syndrome [online], [retrieved on Dec. 22, 2009], 3 pages. Retrieved from the Internet: <URL: http://www.nlm.nih.gov/medlineplus/ency/article/001180.htm>.
Ninds Kennedy's Disease Information p. [online], [retrieved on Dec. 22, 2009], 2pages. Retrieved from the Internet: <URL: http://www.ninds.nih.gov/disorders/kennedys/kennedys.htm>.
Facts about SMA [online], [retrieved on Dec. 22, 2009], 2 pages. Retrieved from the Internet: <URL: http://www.mdausa.org/publications/fa-sma-qa.html>.
Kumar et al., Journal of Medicinal Chemistry, 1993, 36(22), pp. 3278-3285.
Singh et al., Indian Journal of Chemistry, Section B: Organic Chemistry Including Medicinal Chemistry, 1999, 38B(7), pp. 847-849.
Ubillas et al., Planta Medica, 1999, 65(8), pp. 778-779.
Yasue et al., Yakugaku Zasshi (Journal of the Pharmaceutical Society of Japan), 1973, 93(3), pp. 296-299.
Clinton et al., Journal of Organic Chemistry, 1962, vol. 27, pp. 2800-2807.
Giacopello et al., Tetrahedron Letters, 1994, 35(36), pp. 6643-6646.
Bi et al., Steroids, 1992, 57(7), pp. 306-312.
Schanzer et al., Journal of Steroid Biochemistry, 1990, 36(1-2), pp. 153-174.
Troet et al., Journal of Organic Chemistry, 1980 45(14), pp. 2741-2746.
Derenberg et al., Journal of the Chemical Society [Section] D: Chemical Communications, 1971, vol. 5, pp. 233-234.

(Continued)

*Primary Examiner* — Golam M Shameem
(74) *Attorney, Agent, or Firm* — Virtual Law Partners LLP; Richard G. A. Bone

(57) ABSTRACT

The invention provides non-steroidal ligands for the glucocorticoid receptor, methods for making non-steroidal ligands of the glucocorticoid receptor, compositions of non-steroidal ligands of the glucocorticoid receptor and methods of using non-steroidal ligands and compositions of non-steroidal ligands of the glucocorticoid receptor for treating or preventing diseases (e.g., obesity, diabetes, depression, neurodegeneration or an inflammatory disease) associated with glucocorticoid binding to the glucocorticoid receptor.

24 Claims, 7 Drawing Sheets

OTHER PUBLICATIONS

Manhas et al., Journal of the Chemical Society [Section] C: Organiz, 1969, vol. 14, pp. 1937-1939.

Ohta et al., Chemical & Pharmaceutical Bulletin, 1968, 16(8), pp. 1487-1497.

Caspi et al., Canadian Journal of Chemistry 1963, 41(9), pp. 2294-2298.

Honda et al., Journal of Medicinal Chemistry 2000, 43(22), pp. 4233-4246.

Honda et al., Journal of Medicinal Chemistry 2000, 43(9), pp. 1886-1877.

Sakurai et al., Biological & Pharmaceutical Bulletin, 1993, 16(2), pp. 142-145.

Duarte et al., Life Sciences, 1992, 50(12), pp. 891-897.

* cited by examiner

Scheme 1

Scheme 2

Scheme 3

Scheme 4

Scheme 5

Scheme 6

Scheme 7 ations of U.S.
NON-STEROIDAL LIGANDS FOR THE GLUCOCORTICOID RECEPTOR, AND COMPOSITIONS THEREOF This application is a continuation application of U.S. patent application Ser. No. 10/972,250, filed on Oct. 22, 2004, now U.S. Pat. No. 7,485,660, which is a divisional application of U.S. patent application Ser. No. 10/350,260, filed on Jan. 22, 2003, now U.S. Pat. No. 6,831,093, which claims benefit of priority to U.S. provisional patent application Ser. Nos. 60/351,484, filed on Jan. 22, 2002 and 60/373,757, filed on Apr. 17, 2002, all of which are incorporated herein by reference in their entirety.

ACKNOWLEDGMENT

This invention was made with government support under DK57574 awarded by the National Institutes of Health. The government has certain rights in the invention.

FIELD OF THE INVENTION

The present invention relates generally to non-steroidal ligands of the glucocorticoid receptor, methods for making non-steroidal ligands compositions of non-steroidal ligands, and methods for using non-steroidal ligands, and methods for using compositions of non-steroidal ligands. More specifically, the present invention relates to derivatives of Wieland-Miescher ketone, methods for making derivatives of Wieland-Miescher ketone, compositions of derivatives of Wieland-Miescher ketone, methods for using derivatives of Wieland-Miescher ketone, and methods for using compositions of derivatives of Wieland-Miescher ketone.

BACKGROUND OF THE INVENTION

The glucocorticoid receptor is a member of the steroid thyroid nuclear hormone receptor superfamily, which includes, but is not limited to, mineral corticoid, androgen, progesterone and estrogen receptors. The glucocorticoid receptor is activated in vivo by binding of natural agonists such as cortisol and corticosterone. The glucocorticoid receptor may also be activated by binding of synthetic agonists such as dexamethasone, prednisone and prednisilone. Many synthetic antagonists of glucocorticoid receptors (e.g., RU-486) are also known.

Since the presence or absence of ligand binding to the glucocorticoid receptor may have profound physiological consequences (e.g., lead to Cushing's syndrome or Addison's disease), drugs that target the glucocorticoid receptor are clinically relevant. Consequently, selective glucocorticoid receptor ligands that either activate (i.e., agonists) or inactivate (i.e., antagonists) glucocorticoid mediated response are compounds of pharmaceutical interest.

The glucocorticoid receptor, when activated by ligand, mediates biological processes (e.g., metabolism, electrolyte balance, organ and tissue systems, etc.) by binding to specific regulatory DNA sequences (i.e., response elements) in the promoter of cortisol-regulated genes. The glucocorticoid receptor may thus activate or repress transcription of cortisol-regulated genes. At least three different response elements exist for glucocorticoid receptor regulation: (1) the glucocorticoid response element (GRE); (2) an AP-1/GRE; and (3) a NFκB/GRE. Agonist binding to the glucocorticoid receptor leads to transcriptional activation of the GRE and transcriptional repression of AP-1/GRE and NFκB/GR.

Currently available drugs that bind to the glucocorticoid receptor are typically cortisol analogues, which produce undesired side effects that are caused by: (1) unselective binding to other steroid receptors; and (2) failure to disassociate the different response elements when binding to the glucocorticoid receptor. Thus, there exists a need for compounds that selectively bind to the glucocorticoid receptor and selectively disassociate the different response elements of the glucocorticoid receptor.

SUMMARY OF THE INVENTION

The present invention addresses these and other needs by providing non-steroidal ligands for the glucocorticoid receptor, methods for making non-steroidal ligands of the glucocorticoid receptor, compositions of non-steroidal ligands of the glucocorticoid receptor and methods of using non-steroidal ligands and compositions of non-steroidal ligands of the glucocorticoid receptor for treating or preventing diseases (e.g., obesity, diabetes, depression, neurodegeneration or an inflammatory disease) associated with glucocorticoid binding to the glucocorticoid receptor. In principle, the current invention allows for the preparation of either agonist or antagonist compounds and either or both of these pharmacological modes of action may be useful for certain therapeutic treatments.

The compounds of the instant invention include a carbocyclic ring system, which may be unsaturated and may be annelated with a heterocyclic ring. In particular, the carbocyclic ring systems may be an indan (i.e., a six membered carbocyclic ring fused with a five membered carbocyclic ring), a dehydro-decalin (i.e., a six membered carbocyclic ring fused with a six membered carbocyclic ring) or a dehydro [4.5.0] bicyclo undecane (i.e., a six membered carbocyclic ring fused with a seven membered carbocyclic ring) ring system. When the carbocyclic ring system comprises a carbocyclic ring system annelated with a heterocyclic ring, the heterocyclic ring is typically attached to the six membered ring fragment—say of an indan or a dehydro-decalin—and has at least one oxygen, nitrogen or sulfur atom.

In a first aspect, the present invention provides compounds of formula (I):

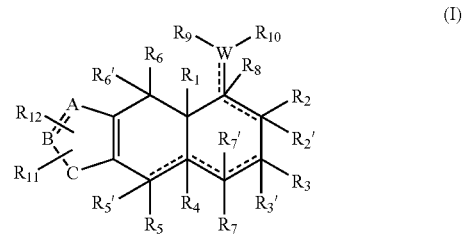

or a pharmaceutically available salt, solvate or hydrate thereof wherein:

A, B and C are independently carbon, nitrogen, oxygen or sulfur provided that at least one of A, B and C is nitrogen, oxygen or sulfur and that no more than one of A, B and C are oxygen or sulfur;

W is carbon, oxygen, nitrogen, or sulfur and, when W is other than carbon and nitrogen, one or more of $R_8$, $R_9$ and $R_{10}$ is absent so that a normal valence on W is maintained;

$R_1$ is hydrogen, alkyl, substituted alkyl, acyl, substituted acyl, acylamino, substituted acylamino, amino, alkylamino, substituted alkylamino, dialkylamino, substituted dialkylamino, alkoxycarbonyl, substituted alkoxycarbonyl, arylalkyl, substituted arylalkyl, aryloxycarbonyl, substituted aryloxycarbonyl, carbamoyl, substituted carbamoyl, carboxy, cyano, halo, heteroalkyl or substituted heteroalkyl, heteroarylalkyl or substituted heteroarylalkyl;

$R_2$, $R_3$, $R_5$, $R_6$, $R_6'$, and $R_7$ are independently hydrogen, alkyl, substituted alkyl, acyl, substituted acyl, acylamino, substituted acylamino, alkoxy, substituted alkoxy, amino, alkylamino, substituted alkylamino, dialkylamino, substituted dialkylamino, alkylsulfonyl, substituted alkylsulfonyl, alkylsulfinyl, substituted alkylsulfinyl, alkylthio, substituted alkylthio, alkoxycarbonyl, substituted alkoxycarbonyl, arylalkyl, substituted arylalkyl, aryloxycarbonyl, substituted aryloxycarbonyl, carbamoyl, substituted carbamoyl, carboxy, cyano, halo, heteroalkyl, substituted heteroalkyl, heteroarylalkyl, substituted heteroarylalkyl or hydroxy;

$R_2'$, $R_3'$, $R_5'$, $R_7'$ and $R_8$ are absent or are independently hydrogen, alkyl, substituted alkyl, acyl, substituted acyl, acylamino, substituted acylamino, alkoxy, substituted alkoxy, amino, alkylamino, substituted alkylamino, dialkylamino, substituted dialkylamino, alkylsulfonyl, substituted alkylsulfonyl, alkylsulfinyl, substituted alkylsulfinyl, alkylthio, substituted alkylthio, alkoxycarbonyl, substituted alkoxycarbonyl, arylalkyl, substituted arylalkyl, aryloxycarbonyl, substituted aryloxycarbonyl, carbamoyl, substituted carbamoyl, carboxy, cyano, halo, heteroalkyl, substituted heteroalkyl, heteroarylalkyl, substituted heteroarylalkyl or hydroxy;

$R_4$ is absent or is hydrogen, alkyl, substituted alkyl, acyl, substituted acyl, acylamino, substituted acylamino, amino, alkylamino, substituted alkylamino, dialkylamino, substituted dialkylamino, alkoxycarbonyl, substituted alkoxycarbonyl, arylalkyl, substituted arylalkyl, aryloxycarbonyl, substituted aryloxycarbonyl, carbamoyl, substituted carbamoyl, carboxy, cyano, halo, heteroalkyl, substituted heteroalkyl, heteroarylalkyl or substituted heteroarylalkyl;

$R_9$ is hydrogen, alkyl, substituted alkyl, alkoxy, substituted alkoxy, amino, alkylamino, substituted alkylamino, dialkylamino, substituted dialkylamino, carboxy, cyano, halo, oxo, thio, hydroxy or is absent;

$R_{10}$ is hydrogen, alkyl, substituted alkyl, acyl, substituted acyl, alkoxycarbonyl, substituted alkoxycarbonyl, aryl, substituted aryl, arylalkyl, substituted arylalkyl, aryloxycarbonyl, substituted aryloxycarbonyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl, substituted heteroarylalkyl, or is absent;

$R_{10}$ and $R_2$ may bond directly to one another to form a ring, and an additional ring such as a benzene ring, which may itself be substituted with an alkyl, alkoxy, halo, alkyl, substituted alkyl, acyl, substituted acyl, cycloalkyl, or substituted cycloalkyl, may fuse to the bond between $R_{10}$ and $R_2$; and $R_{11}$ and $R_{12}$ are independently hydrogen, alkyl, substituted alkyl, acyl, substituted acyl, acylamino, substituted acylamino, alkoxy, substituted alkoxy, amino, alkylamino, substituted alkylamino, dialkylamino, substituted dialkylamino, alkylsulfonyl, substituted alkylsulfonyl, alkylsulfinyl, substituted alkylsulfinyl, alkylthio, substituted alkylthio, alkoxycarbonyl, substituted alkoxycarbonyl, aryl, substituted aryl, arylalkyl, substituted arylalkyl, aryloxycarbonyl, substituted aryloxycarbonyl, carbamoyl, substituted carbamoyl, carboxy, cyano, halo, oxo, thio, heteroalkyl, substituted heteroalkyl, heteroaryl, substituted heteroaryl, heteroarylalkyl, substituted heteroarylalkyl or hydroxy.

The bonds in formula (I) that are shown with single and dashed lines are intended to represent alternative forms of the structure. That is, one or more, but preferably one, such bonds may be a double bond provided that normal valences of the atoms in the rings are satisfied.

In a second aspect, the present invention provides compositions of compounds of the invention. The compositions generally comprise one or more compounds of the invention, pharmaceutically acceptable salts, hydrates or solvates thereof and a pharmaceutically acceptable diluent, carrier, excipient and adjuvant. The choice of diluent, carrier, excipient and adjuvant will depend upon, among other factors, the desired mode of administration.

In a third aspect, the present invention provides methods for treating or preventing obesity, diabetes, depression, neurodegeneration or an inflammatory disease. The methods generally involve administering to a patient in need of such treatment or prevention a therapeutically effective amount of a compound and/or composition of the invention.

In a fourth aspect, the current invention provides compositions for treating or preventing obesity, diabetes, depression, neurodegeneration or an inflammatory disease in a patient in need of such treatment or prevention.

In a fifth aspect the current invention provides methods for selectively modulating the activation, repression, agonism and antagonism effects of the glucocorticoid receptor in a patient. The methods generally involve administering to patient in need of such treatment a therapeutically effective amount of a compound or composition of the invention.

DETAILED DESCRIPTION OF THE INVENTION

Definitions

Figure 1:
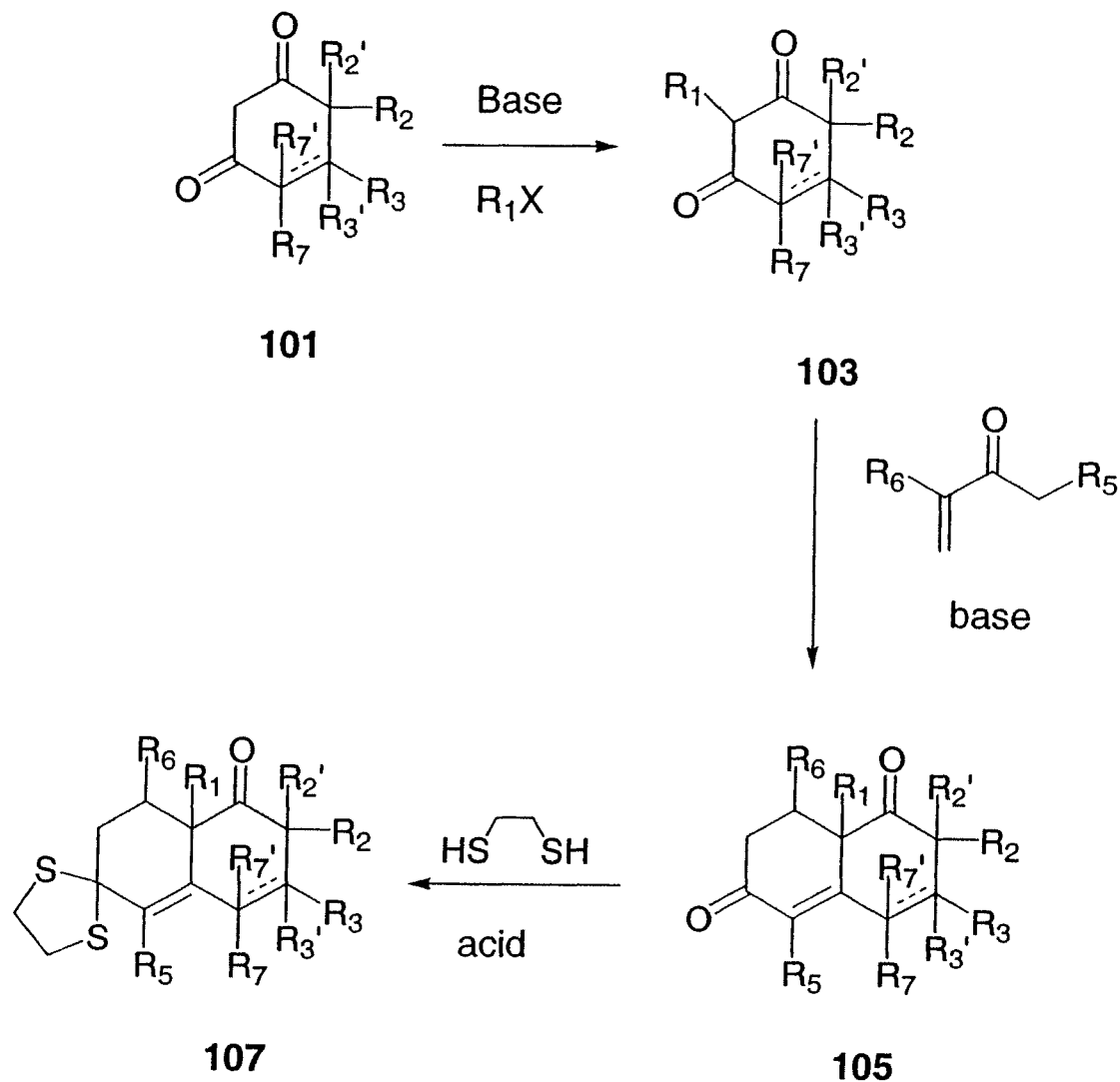
FIG. 1 shows synthesis Scheme 1, for a preferred synthetic route to a ketone intermediate used for synthesis of the compounds of structural formula (I).

"Compounds of the invention" refers to compounds encompassed by structural Formula (I) disclosed herein and includes any specific compounds within that formula whose structure is disclosed herein. The compounds of the invention may be identified either by chemical structure and/or chemical name. When the chemical structure and chemical name conflict, the chemical structure is determinative of the identity of the compound. The compounds of the invention may contain one or more chiral centers and/or double bonds and therefore, may exist as stereoisomers, such as double-bond isomers (i.e., geometric isomers), enantiomers or diastereomers. Accordingly, the chemical structures depicted herein encompass all possible enantiomers and stereoisomers of the illustrated compounds including the stereoisomerically pure form (e.g., geometrically pure, enantiomerically pure or diastereomerically pure), and enantiomeric and stereoisomeric mixtures. Enantiomeric and stereoisomeric mixtures can be resolved into their component enantiomers or stereoisomers using separation techniques or chiral synthesis techniques well known to an artisan of ordinary skill. The compounds of the invention may also exist in several tautomeric forms including the enol form, the keto form and mixtures thereof. Accordingly, the chemical structures depicted herein encompass all possible tautomeric forms of the illustrated compounds.

The compounds of the invention also include isotopically labeled compounds where one or more atoms have an atomic mass different from the most abundant atomic mass normally found in nature for given atom. Examples of isotopes that may be incorporated into the compounds of the invention include, but are not limited to, $^2$H, $^3$H, $^{13}$C, $^{14}$C, $^{15}$N, $^{17}$O, $^{18}$O, $^{31}$P, $^{32}$P, $^{35}$S, $^{18}$F and $^{36}$Cl.

Furthermore it should be understood that, when partial structures of the compounds of the invention or precursors thereto are illustrated, brackets of dashes indicate the point of attachment of the partial structure to the rest of the molecule.

"Alkyl" refers to a saturated or unsaturated, branched, straight-chain or cyclic monovalent hydrocarbon radical derived by the removal of one hydrogen atom from a single carbon atom of a parent alkane, alkene or alkyne. Typical alkyl groups include, but are not limited to, methyl; ethyls such as ethanyl, ethenyl, ethynyl; propyls such as propan-1-yl, propan-2-yl, cyclopropan-1-yl, prop-1-n–1-yl, prop-1-en-2-yl, prop-2-en-1-yl (allyl), cycloprop-1-en-1-yl; cycloprop-2-en-1-yl, prop-1-yn-1-yl, prop-2-yn-1-yl, etc.; butyls such as butan-1-yl, butan-2-yl, 2-methyl-propan-1-yl, 2-methyl-propan-2-yl, cyclobutan-1-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, but-1-yn-1-yl, but-1-yn-3-yl, but-3-yn-1-yl, etc.; and the like.

The term "alkyl" is specifically intended to include radicals having any degree or level of saturation, i.e., groups having exclusively carbon-carbon single bonds, groups having one or more carbon-carbon double bonds, groups having one or more carbon-carbon triple bonds and groups having mixtures of single, double and triple carbon-carbon bonds. Where a specific level of saturation is intended, the expressions "alkanyl", "alkenyl", and "alkynyl" are used. Preferably, an alkyl group comprises from 1 to 20 carbon atoms, more preferably from 1 to 10 carbon atoms or still more preferably from 1 to 6 carbon atoms.

"Alkanyl" refers to a saturated branched, straight-chain or cyclic alkyl radical derived by the removal of one hydrogen atom from a single carbon atom of a parent alkane. Typical alkanyl groups include, but are not limited to, methanyl; ethanyl; propanyls such as propan-1-yl, propan-2-yl (isopropyl), cyclopropan-1-yl, etc.; butanyls such as butan-1-yl, butan-2-yl (sec-butyl), 2-methyl-propan-1-yl (isobutyl), 2-methyl-propan-2-yl (t-butyl), cyclobutan-1-yl, etc.; and the like.

"Alkenyl" refers to an unsaturated branched, straight-chain or cyclic alkyl radical having at least one carbon-carbon double bond, derived by the removal of one hydrogen atom from a single carbon atom of a parent alkene. The various groups attached to the double bond(s) may be in either the cis or trans (or E, or Z) conformation about the double bond(s). Typical alkenyl groups include, but are not limited to, ethenyl; propenyls such as prop-len-1-yl, prop-1-en-2-yl, prop-2-en-1-yl (allyl), prop-2-en-2-yl, cycloprop-1-en-1-yl; cycloprop-2-en-1-yl; butenyls such as but-1-en-1-yl, but-1-en-2-yl, 2-methyl-prop-In-1-yl, but-2-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, etc.; penta-2,4-diene, and the like.

"Alkynyl" refers to an unsaturated branched, straight-chain or cyclic alkyl radical having at least one carbon-carbon triple bond, derived by the removal of one hydrogen atom from a single carbon atom of a parent alkyne. Typical alkynyl groups include, but are not limited to, ethynyl; propynyls such as prop-1-yn-1-yl, prop-2-yn-1-yl, etc.; butynyls such as but-1-yn-1-yl, but-1-yn-3-yl, but-3-yn-1-yl, etc.; and the like.

"Acyl" refers to a radical —C(=O)R, where R is hydrogen, alkyl, cycloalkyl, cycloheteroalkyl, aryl, arylalkyl, heteroalkyl, heteroaryl, heteroarylalkyl as defined herein. Representative examples include, but are not limited to formyl, acetyl, cyclohexylcarbonyl, cyclohexylmethylcarbonyl, benzoyl, benzylcarbonyl and the like.

"Acylamino" refers to a radical —NR'C(=O)R, where R' and R are each independently hydrogen, alkyl, cycloalkyl, cycloheteroalkyl, aryl, arylalkyl, heteroalkyl, heteroaryl, heteroarylalkyl, as defined herein. Representative examples include, but are not limited to, formylamino, acetylamino, cyclohexylcarbonylamino, cyclohexylmethyl-carbonylamino, benzoylamino, benzylcarbonylamino and the like.

"Alkylamino" means a radical —NHR where R represents an alkyl or cycloalkyl group as defined herein. Representative examples include, but are not limited to, methylamino, ethylamino, 1-methylethylamino, cyclohexylamino and the like.

"Alkoxy" refers to a radical —OR where R represents an alkyl or cycloalkyl group as defined herein. Representative examples include, but are not limited to, methoxy, ethoxy, propoxy, butoxy, cyclohexyloxy and the like.

"Alkoxycarbonyl" refers to a radical —C(O)-alkoxy where alkoxy is as defined herein.

"Alkylsulfonyl" refers to a radical S(=O)$_2$R where R is an alkyl or cycloalkyl group as defined herein. Representative examples include, but are not limited to, methylsulfonyl, ethylsulfonyl, propylsulfonyl, butylsulfonyl and the like.

"Alkylsulfinyl" refers to a radical —S(=O)R where R is an alkyl or cycloalkyl group as defined herein. Representative examples include, but are not limited to, methylsulfinyl, ethylsulfinyl, propylsulfinyl, butylsulfinyl and the like.

"Alkylthio" refers to a radical —SR where R is an alkyl or cycloalkyl group as defined herein that may be optionally substituted as defined herein. Representative examples include, but are not limited to, methylthio, ethylthio, propylthio, butylthio, and the like.

"Amino" refers to the radical —NH$_2$.

"Aryl" refers to a monovalent aromatic hydrocarbon radical derived by the removal of one hydrogen atom from a single carbon atom of a parent aromatic ring system. Typical aryl groups include, but are not limited to, groups derived from fused ring systems that comprise one or more aromatic rings, or conjugated ring systems, such as aceanthrylene, acenaphthylene, acephenanthrylene, anthracene, azulene, benzene, chrysene, coronene, fluoranthene, heptaphene, hexacene, hexaphene, as-indacene, s-indacene, indene, naphthalene (hexylene), octacene, octaphene, octalene, ovalene, pentacene, pentalene, pentaphene, perylene, phenalene, phenanthrene, picene, pleiadene, pyrene, pyranthrene, rubicene, tetraphenylene, triphenylene, trinaphthalene and the like. Additionally, aryl groups include fused ring systems containing at least one aromatic ring and at least one partially saturated ring, such as fluorene, indane, biphenylene and the like. Preferably, an aryl group comprises from 6 to 20 carbon atoms, more preferably between 6 to 12 carbon atoms.

"Arylalkyl" refers to an acyclic alkyl radical in which one of the hydrogen atoms bonded to a carbon atom, typically a terminal or sp³ hybridized carbon atom, is replaced with an aryl group. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. Where specific alkyl moieties are intended, the nomenclature arylalkanyl, arylalkenyl and/or arylalkynyl is used. Preferably, an arylalkyl group is ($C_6$-$C_{30}$) arylalkyl, e.g., the alkanyl, alkenyl or alkynyl moiety of the arylalkyl group is ($C_1$-$C_{10}$) and the aryl moiety is ($C_6$-$C_{20}$), more preferably, an arylalkyl group is ($C_6$-$C_{20}$) arylalkyl, e.g., the alkanyl, alkenyl or alkynyl moiety of the arylalkyl group is ($C_1$-$C_8$) and the aryl moiety is ($C_6$-$C_{12}$).

"Arylalkyloxy" refers to an —O-arylalkyl radical where arylalkyl is as defined herein.

"Aryloxycarbonyl" refers to a radical —C(=O)—O-aryl where aryl is as defined herein.

"Carbamoyl" refers to the radical —C(=O)N(R)$_2$ where each R group is independently hydrogen, alkyl, cycloalkyl or aryl as defined herein, which may be optionally substituted as defined herein.

"Carboxy" means the radical —C(=O)OH.

"Cyano" means the radical —CN.

"Cycloalkyl" refers to a saturated or unsaturated cyclic alkyl radical. Where a specific level of saturation is intended, the nomenclature "cycloalkanyl" or "cycloalkenyl" is used. Typical cycloalkyl groups include, but are not limited to, groups derived from cyclopropane, cyclobutane, cyclopentane, cyclohexane, and the like. Preferably, the cycloalkyl group is $C_3$-$C_{10}$ cycloalkyl, more preferably $C_3$-$C_7$ cycloalkyl.

"Cycloheteroalkyl" refers to a saturated or unsaturated cyclic alkyl radical in which one or more carbon atoms (and any associated hydrogen atoms) are independently replaced with the same or different heteroatom. Typical heteroatoms to replace the carbon atom(s) include, but are not limited to, N, P, O, S, Si, etc. Where a specific level of saturation is intended, the nomenclature "cycloheteroalkanyl" or "cycloheteroalkenyl" is used. Typical cycloheteroalkyl groups include, but are not limited to, groups derived from epoxides, imidazolidine, morpholine, piperazine, piperidine, pyrazolidine, pyrrolidine, quinuclidine, and the like.

"Cycloheteroalkyloxycarbonyl" refers to a radical C(=O)—OR where R is cycloheteroalkyl as defined herein.

"Dialkylamino" means a radical —NRR' where R and R' independently represent an alkyl or cycloalkyl group as defined herein. Representative examples include, but are not limited to dimethylamino, methyl-ethylamino, di-(1-methylethyl)amino, cyclohexyl-methyl amino, cyclohexyl-ethyl amino, cyclohexyl-propyl amino, and the like.

"Halo" means fluoro, chloro, bromo, or iodo.

"Heteroalkyloxy" means an —O-heteroalkyl radical where heteroalkyl is as defined herein.

"Heteroalkyl, Heteroalkanyl, Heteroalkenyl, Heteroalkynyl" refer to alkyl, alkanyl, alkenyl and alkynyl groups, respectively, in which one or more of the carbon atoms (and any associated hydrogen atoms) are each independently replaced with the same or different heteroatomic groups. Typical heteroatomic groups include, but are not limited to, —O—, —S—, —O—O—, —S—S—, —O—S—, —NR'—, =N—N=, —N=N—, —N=N—NR'—, —PH—, —P(O)$_2$, P(O)$_2$—, —S(O), —S(O)$_2$, —SnH$_2$— and the like, wherein R' is hydrogen, alkyl, substituted alkyl, cycloalkyl, substituted cycloalkyl, aryl or substituted aryl.

"Heteroaryl" refers to a monovalent heteroaromatic radical derived by the removal of one hydrogen atom from a single atom of a parent heteroaromatic ring system. Typical heteroaryl groups include, but are not limited to, groups derived from acridine, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. Preferably, the heteroaryl group has from 5-20 non-hydrogen atoms, with 5-10 non-hydrogen atoms being particularly preferred. Preferred heteroaryl groups are those derived from thiophene, pyrrole, benzothiophene, benzofuran, indole, pyridine, quinoline, imidazole, oxazole and pyrazine.

"Heteroaryloxycarbonyl" refers to a radical —C(=O)OR where R is heteroaryl as defined herein.

"Heteroarylalkyl" refers to an acyclic alkyl radical in which one of the hydrogen atoms bonded to a carbon atom, typically a terminal or sp³ hybridized carbon atom, is replaced with a heteroaryl group. Where specific alkyl moieties are intended, the nomenclature heteroarylalkanyl, heteroarylalkenyl and/or heterorylalkynyl is used. Preferably, the heteroarylalkyl radical has 6-30 non-hydrogen atoms, e.g., the alkanyl, alkenyl or alkynyl moiety of the heteroarylalkyl is $C_{1-10}$ and the heteroaryl moiety is a 5-20 membered heteroaryl, more preferably, a 6-20 membered heteroarylalkyl, e.g., the alkanyl, alkenyl or alkynyl moiety of the heteroarylalkyl is 1-8 membered and the heteroaryl moiety is a 5-12 membered heteroaryl.

"Hydroxy" means the radical —OH.

"Oxo" means the divalent radical =O.

"Prodrug" refers to a pharmacologically inactive derivative of a drug molecule that requires a transformation within the body to release the active drug.

"Promoiety" refers to a form of protecting group that when used to mask a functional group within a drug molecule converts the drug into a prodrug. Typically, the promoiety will be attached to the drug via bond(s) that are cleaved by enzymatic or non-enzymatic means in vivo. Ideally, the promoiety is rapidly cleared from the body upon cleavage from the prodrug.

"Protecting group" refers to a grouping of atoms that when attached to a reactive group in a molecule masks, reduces or prevents that reactivity. Examples of protecting groups can be found in Green et al., "Protective Groups in Organic Chemistry", (Wiley, 2$^{nd}$ ed. 1991) and Harrison et al., "Compendium of Synthetic Organic Methods", Vols. 1-8 (John Wiley and Sons, 1971-1996). Representative amino protecting groups include, but are not limited to, formyl, acetyl, trifluoroacetyl, benzyl, benzyloxycarbonyl" ("CBZ"), tert-butoxycarbonyl ("Boc"), trimethylsilyl ("TMS"), 2-trimethylsilylethanesulfonyl ("SES"), trityl and substituted trityl groups, allyloxycarbonyl, 9-fluorenylmethyloxycarbonyl ("FMOC"), nitro-veratryloxycarbonyl ("NVOC") and the like. Representative hydroxy protecting groups include, but are not limited to, those where the hydroxy group is either acylated or alkylated such as benzyl, and trityl ethers as well as alkyl ethers, tetrahydropyranyl ethers, trialkylsilyl ethers and allyl ethers.

"Substituted" refers to a group in which one or more hydrogen atoms are each independently replaced with the same or different substituent(s). Typical substituents include, but are not limited to, —X, —R$^{14}$, —O—, =O, —OR$^{14}$, —SR$^{14}$, —S$^-$; =S, —NR$^{14}$R$^{15}$, =NR$^{14}$, —CX$_3$, —CF$_3$, CN, —OCN, SCN, —NO, —NO$_2$, =N$_2$, —N$_3$, —(O)$_2$O$^-$, —S(O)$_2$OH, —S(O)$_2$R$^{14}$, —OS(O$_2$)O$^-$, —OS(O)$_2$R$^{14}$, —P(O)(O)$_2$, —P(O)(OR$^{14}$)(O$^-$), —OP(O)(OR$^{14}$)(OR$^{15}$), C(O)R$^{14}$, C(S)R$^{14}$, C(O)OR$^{14}$, —(O)NR$^{14}$R$^{15}$, —(O)O—, —C(S)OR$^{14}$, —NR$^{16}$C(O)NR$^{14}$R$^{15}$, —NR$^{16}$C(S)NR$^{14}$R$^{15}$, —NR$^{17}$C(NR$^{16}$)NR$^{14}$R$^{15}$ and —C(NR$^{16}$)NR$^{14}$R$^{15}$, where each X is independently a halogen; each R$^{14}$, R$^{15}$, R$^{16}$ and R$^{17}$ are independently hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl, substituted heteroarylalkyl, —NR$^{18}$R$^{19}$, —C(O)R$^{18}$ or —S(O)$_2$R$^{18}$ or optionally R$^{18}$ and R$^{19}$ together with the atom to which they are both attached form a cycloheteroalkyl or substituted cycloheteroalkyl ring; and R$^{18}$ and R$^{19}$ are independently hydrogen, alkyl, substituted alkyl, aryl, substituted alkyl, arylalkyl, substituted alkyl, cycloalkyl, substituted alkyl, cycloheteroalkyl, substituted cycloheteroalkyl, heteroalkyl, substituted heteroalkyl, heteroaryl, substituted heteroaryl, heteroarylalkyl or substituted heteroarylalkyl.

"Thio" means the radical —SH.

"Valence" refers to the number of bonds that an atom forms. In organic chemistry this ordinarily means that no unpaired electrons are associated with an atom in its normal valence when bonded in a chemically stable molecule. Thus, for example, the normal valence of carbon is 4, hydrogen is 1, nitrogen is 3, oxygen is 2, sulfur is 2, and the halogens each have a normal valence of 1.

Reference will now be made in detail to preferred embodiments of the invention. While the invention will be described in conjunction with the preferred embodiments, it will be understood that it is not intended to limit the invention to those preferred embodiments. To the contrary, it is intended to cover alternatives, modifications, and equivalents as may be included within the spirit and scope of the invention as defined by the appended claims.

The Compounds of the Invention

The compounds of the invention include compounds of formula (I):

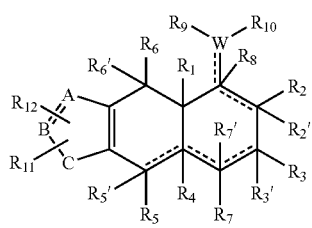

(I)

or a pharmaceutically available salt, solvate of hydrate thereof wherein:

A, B and C are independently carbon, nitrogen, oxygen or sulfur provided that at least one of A, B and C is nitrogen, oxygen or sulfur and that no more than one of A, B and C are oxygen or sulfur;

W is carbon, oxygen, nitrogen, or sulfur and when W is other than carbon and nitrogen, one or more of R$_8$, R$_9$ and R$_{10}$ is absent so that a normal valence on W is maintained;

R$_1$ is hydrogen, alkyl, substituted alkyl, acyl, substituted acyl, acylamino, substituted acylamino, amino, alkylamino, substituted alkylamino, dialkylamino, substituted dialkylamino, alkoxycarbonyl, substituted alkoxycarbonyl, arylalkyl, substituted arylalkyl, aryloxycarbonyl, substituted aryloxycarbonyl, carbamoyl, substituted carbamoyl, carboxy, cyano, halo, heteroalkyl or substituted heteroalkyl, heteroarylalkyl or substituted heteroarylalkyl;

R$_2$, R$_3$, R$_5$, R$_6$, R$_6$', and R$_7$ are independently hydrogen, alkyl, substituted alkyl, acyl, substituted acyl, acylamino, substituted acylamino, alkoxy, substituted alkoxy, amino, alkylamino, substituted alkyl amino, dialkylamino, substituted dialkylamino, alkylsulfonyl, substituted alkylsulfonyl, alkylsulfinyl, substituted alkylsulfinyl, alkylthio, substituted alkylthio, alkoxycarbonyl, substituted alkoxycarbonyl, arylalkyl, substituted arylalkyl, aryloxycarbonyl, substituted aryloxycarbonyl, carbamoyl, substituted carbamoyl, carboxy, cyano, halo, heteroalkyl, substituted heteroalkyl, heteroarylalkyl, substituted heteroarylalkyl or hydroxy;

R$_2$', R$_3$', R$_5$', R$_7$' and R$_8$ are absent or are independently hydrogen, alkyl, substituted alkyl, acyl, substituted acyl, acylamino, substituted acylamino, alkoxy, substituted alkoxy, amino, alkylamino, substituted alkylamino, dialkylamino, substituted dialkylamino, alkylsulfonyl, substituted alkylsulfonyl, alkylsulfinyl, substituted alkylsulfinyl, alkylthio, substituted alkylthio, alkoxycarbonyl, substituted alkoxycarbonyl, arylalkyl, substituted arylalkyl, aryloxycarbonyl, substituted aryloxycarbonyl, carbamoyl, substituted carbamoyl, carboxy, cyano, halo, heteroalkyl, substituted heteroalkyl, heteroarylalkyl, substituted heteroarylalkyl or hydroxy;

R$_4$ is absent or is hydrogen, alkyl, substituted alkyl, acyl, substituted acyl, acylamino, substituted acylamino, amino, alkylamino, substituted alkylamino, dialkylamino, substituted dialkylamino, alkoxycarbonyl, substituted alkoxycarbonyl, arylalkyl, substituted arylalkyl, aryloxycarbonyl, substituted aryloxycarbonyl, carbamoyl, substituted carbamoyl, carboxy, cyano, halo, heteroalkyl, substituted heteroalkyl, heteroarylalkyl or substituted heteroarylalkyl;

R$_9$ is hydrogen, alkyl, substituted alkyl, alkoxy, substituted alkoxy, amino, alkylamino, substituted alkylamino, dialkylamino, substituted dialkylamino, carboxy, cyano, halo, oxo, thio, hydroxy or is absent;

R$_{10}$ is hydrogen, alkyl, substituted alkyl, acyl, substituted acyl, alkoxycarbonyl, substituted alkoxycarbonyl, aryl, substituted aryl, arylalkyl, substituted arylalkyl, aryloxycarbonyl, substituted aryloxycarbonyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl, substituted heteroarylalkyl, or is absent;

R$_{10}$ and R$_2$ may bond directly to one another to form a ring, and an additional ring such as a benzene ring, which may itself be substituted with an alkyl, alkoxy, halo, alkyl, substituted alkyl, acyl, substituted acyl, cycloalkyl, or substituted cycloalkyl, may fuse to the bond between R$_{10}$ and R$_2$; and R$_{11}$ and R$_{12}$ are independently hydrogen, alkyl, substituted alkyl, acyl, substituted acyl, acylamino, substituted acylamino, alkoxy, substituted alkoxy, amino, alkylamino, substituted alkylamino, dialkylamino, substituted dialkylamino, alkylsulfonyl, substituted alkylsulfonyl, alkylsulfinyl, substituted alkylsulfinyl, alkylthio, substituted alkyl thio, alkoxycarbonyl, substituted alkoxycarbonyl, aryl, substituted aryl, arylalkyl, substituted arylalkyl, aryloxycarbonyl, substituted aryloxycarbonyl, carbamoyl, substituted carbamoyl, carboxy, cyano, halo, oxo, thio, heteroalkyl, substituted heteroalkyl, heteroaryl, substituted heteroaryl, heteroarylalkyl, substituted heteroarylalkyl or hydroxy.

The bonds in formula (I) that are shown with single and dashed lines are intended to represent alternative forms of the structure. That is, one or more, but preferably one, such bonds may be a double bond provided that normal valences of the atoms in the rings are satisfied. To the extent it is necessary, when maintaining the valences of ring carbon atoms that are bonded to one another by a double bond, a ring-substituent attached to one or more such ring carbon atoms may be absent.

The present invention also includes compounds of structural formula (II):

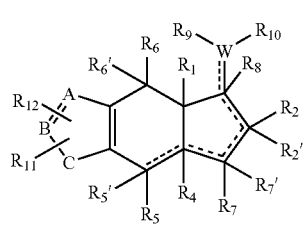

(II)

or a pharmaceutically available salt, solvate or hydrate thereof wherein $R_1$, $R_2$, $R_4$, $R_5$, $R_5'$, $R_6$, $R_6'$, $R_7$, $R_7'$, $R_8$, $R_9$, $R_{10}$, $R_{11}$, $R_{12}$, A, B and C, and W, are as previously defined for formula (f), and $R_2'$ is defined in the same manner as $R_5'$ and $R_7'$ were previously defined for formula (I), and the bonds with single and dashed lines indicate alternative isomeric forms as discussed hereinabove.

The present invention also includes compounds of structural formula (III):

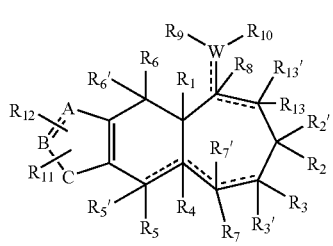

(III)

or a pharmaceutically available salt, solvate or hydrate thereof, wherein $R_1$, $R_2$, $R_2'$, $R_3$, $R_4$, $R_5$, $R_5'$, $R_6$, $R_6'$, $R_7$, $R_7'$, $R_8$, $R_9$, $R_{10}$, $R_{11}$, $R_{12}$, A, B and C, and W are as previously defined in formula (J) and $R_3'$, $R_{13}$ and $R_{13}'$ are defined in the same manner as $R_2$, $R_2'$, $R_3$, $R_5$, $R_6$, $R_7$ and $R_8$ were previously defined in formula (I), and the bonds with single and dashed lines indicate alternative isomeric forms, as discussed hereinabove, and wherein $R_{10}$ and $R_{13}$ (instead of $R_2$) may bond directly to one another to form a ring, and an additional ring may fuse to the bond between $R_{10}$ and $R_{13}$.

In one embodiment of compounds of structural formulae (I), (II) and (III), A, B and C are carbon or nitrogen. Preferably, A is carbon and B and C are nitrogen.

In another embodiment of compounds of structural formulae (I), (II) and (III), A, B and C are carbon, nitrogen or sulfur. Preferably, A is sulfur, B is carbon and C is nitrogen.

In still another embodiment of compounds of structural formulae (I), (II) and (III), A, B and C are carbon, nitrogen or oxygen. Preferably, A is carbon, B is oxygen and C is nitrogen or A is carbon, B is nitrogen and C is oxygen.

In a preferred embodiment of compounds of structural formulae (I), (II) and (III), W is carbon.

In another embodiment of compounds of structural formulae (I), (II) and (III), W is oxygen and bonds with a double bond to the ring carbon atom to which it is attached, and $R_8$, $R_9$ and $R_{10}$ are absent.

In one preferred embodiment of compounds of structural formulae (I), (II) and (III), $R_1$ and $R_4$ are independently hydrogen, alkyl, substituted alkyl, acyl, substituted acyl, alkoxycarbonyl, substituted alkoxycarbonyl, carboxy, cyano, carbamoyl, substituted carbamoyl, heteroalkyl or substituted heteroarylalkyl. Preferably, $R_1$ and $R_4$ are independently hydrogen, alkyl or substituted alkyl. More preferably, $R_1$ and $R_4$ are independently hydrogen or methyl.

In one embodiment of compounds of structural formula (I), $R_2$, $R_2'$, $R_3$, $R_5$, $R_6$, $R_6'$, $R_7$ and $R_9$ are independently hydrogen, alkyl, substituted alkyl, acyl, substituted acyl, alkoxy, substituted alkoxy, amino, alkoxycarbonyl, substituted alkoxycarbonyl, carbamoyl, substituted carbamoyl, carboxy, cyano, halo, heteroalkyl, substituted heteroalkyl or hydroxy. Preferably, $R_2$, $R_2'$, $R_3$, $R_5$, $R_6$, $R_6'$, $R_7$ and $R_8$ are independently hydrogen, alkanyl or substituted alkanyl. More preferably, $R_2$, $R_2'$ $R_3$, $R_5$, $R_6$, $R_6'$, $R_7$ and $R_8$ are hydrogen or methyl.

In an embodiment of compounds of structural formula (II), $R_2$, $R_5$, $R_6$, $R_6'$, $R_7$ and $R_8$ are independently hydrogen, alkyl, substituted alkyl, acyl, substituted acyl, alkoxy, substituted alkoxy, amino, alkoxycarbonyl, substituted alkoxycarbonyl, carbamoyl, substituted carbamoyl, carboxy, cyano, halo, heteroalkyl, substituted heteroalkyl or hydroxy. Preferably, $R_2$, $R_5$, $R_6$, $R_6'$, $R_7$ and $R_8$ are independently hydrogen, alkanyl or substituted alkanyl. More preferably, $R_2$, $R_2'$, $R_5$, $R_6$, $R_6'$, $R_7$ and $R_8$ are hydrogen or methyl.

In an embodiment of compounds of structural formula (III), $R_2$, $R_2'$, $R_3$, $R_3'$, $R_5$, $R_6$, $R_6'$, $R_7$, $R_8$, $R_{13}$ and $R_{13}'$ are independently hydrogen, alkyl, substituted alkyl, acyl, substituted acyl, alkoxy, substituted alkoxy, amino, alkoxycarbonyl, substituted alkoxycarbonyl, carbamoyl, substituted carbamoyl, carboxy, cyano, halo, heteroalkyl, substituted heteroalkyl or hydroxy. Preferably, $R_2$, $R_2'$, $R_3$, $R_5$, $R_6$, $R_6'$, $R_7$, $R_8$, $R_{13}$ and $R_{13}'$ are independently hydrogen, alkanyl or substituted alkanyl. More preferably, $R_2$, $R_2'$, $R_3$, $R_5$, $R_6$, $R_6'$, $R_7$, $R_8$, $R_{13}$ and $R_{13}'$ are hydrogen or methyl.

In an embodiment of compounds of structural formulae (I), (II) and (III), $R_4$ and $R_5'$ are absent. In another embodiment of compounds of structural formulae (I), (II) and (III), $R_4$ and $R_7'$ are absent. In another embodiment of compounds of structural formulae (I) and (III), $R_3'$ and $R_7'$ are absent. In another embodiment of compounds of structural formulae (I) and (DI), $R_3'$ and $R_2'$ are absent.

In an embodiment of compounds of structural formulae (I) and (III), $R_3'$, $R_5'$ and $R_7'$ are independently hydrogen, alkyl, substituted alkyl, acyl, substituted acyl, alkoxy, substituted alkoxy, amino, alkoxycarbonyl, substituted alkoxycarbonyl, carbamoyl, substituted carbamoyl, carboxy, cyano, halo, heteroalkyl, substituted heteroalkyl or hydroxy. Preferably, $R_3'$, $R_5'$ and $R_7'$ are independently hydrogen alkanyl or substituted alkanyl. More preferably, $R_3'$, $R_5'$ and $R_7'$ are hydrogen or methyl.

In an embodiment of compounds of structural formula (II), $R_2'$, $R_5'$ and $R_7'$ are independently hydrogen, alkyl, substituted alkyl, acyl, substituted acyl, alkoxy, substituted alkoxy, amino, alkoxycarbonyl, substituted alkoxycarbonyl, carbamoyl, substituted carbamoyl, carboxy, cyano, halo, heteroalkyl, substituted heteroalkyl or hydroxy. Preferably, $R_2'$, $R_5'$ and $R_7'$ are independently hydrogen, alkanyl or substituted alkanyl. More preferably, $R_2'$, $R_5'$ and $R_7'$ are hydrogen or methyl.

In another embodiment of compounds of structural formulae (I), (II) and (III), $R_9$ is hydrogen, alkoxy, substituted alkoxy, halo, oxo, thio or hydroxy. Preferably, $R_9$ is alkoxy, oxo, hydroxy or is absent.

In still another embodiment of compounds of structural formulae (I), (II) and (III), $R_{10}$ is hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, substituted heteroarylalkyl, or is absent. Preferably, $R_{10}$ is aryl, substituted aryl, heteroaryl or substituted heteroaryl.

In still another embodiment of compounds of structural formulae (I), (II) and (III), $R_{11}$ and $R_{12}$ are independently hydrogen, alkyl, alkoxy, amino, alkylamino, dialkylamino, alkylsulfonyl, alkylsulfinyl, alkylthio, alkoxycarbonyl, substituted alkoxycarbonyl, aryl, substituted aryl, arylalkyl, substituted arylalkyl, carbamoyl, carboxy, cyano, halo, oxo, thio, heteroalkyl, heteroaryl, substituted heteroaryl, heteroarylalkyl, substituted heteroarylalkyl or hydroxy. Preferably, $R_{11}$ and $R_{12}$ are independently hydrogen, aryl, substituted aryl, arylalkyl, substituted arylalkyl, oxo, heteroalkyl, heteroaryl, substituted heteroaryl, heteroarylalkyl, substituted heteroarylalkyl or hydroxy. More preferably, $R_{11}$ and $R_{12}$ are independently hydrogen, aryl or substituted aryl.

In one preferred embodiment of compounds of structural formula (I), $R_1$, $R_2$, $R_2'$, $R_3$, $R_3'$, $R_5$, $R_6$, $R_6'$, $R_7$, $R_7'$ and $R_8$ are hydrogen, alkyl or arylalkyl and $R_4$ and $R_5'$ are absent. In another preferred embodiment, $R_1$ is methyl, $R_2$, $R_2'$, $R_3$, $R_3'$, $R_5$, $R_6$, $R_6'$, $R_7$, $R_7'$ and $R_5$ are hydrogen and $R_4$ and $R_5'$ are absent.

The following embodiments are more specific embodiments of the preceding two preferred embodiments. In one embodiment, $R_9$ is alkoxy, oxo or hydroxy. In another embodiment, $R_{10}$ is aryl, substituted aryl, heteroaryl or substituted heteroaryl. In still another embodiment, A is carbon, B and C are nitrogen, $R_{11}$ is hydrogen and $R_{12}$ is aryl, substituted aryl, heteroaryl or substituted heteroaryl. In still another embodiment, A is sulfur, B is carbon and C is nitrogen. In still another embodiment, A is carbon, B is oxygen and C is nitrogen. In still another embodiment, A is carbon, B is nitrogen and C is oxygen.

In one preferred embodiment of compounds of structural formula (II), $R_1$, $R_2$, $R_2'$, $R_5$, $R_6$, $R_6'$, $R_7$, $R_7'$ and $R_8$ are hydrogen, alkyl or arylalkyl and $R_4$ and $R_5'$ are absent. In another preferred embodiment, $R_1$ is methyl, $R_2$, $R_2'$, $R_5$, $R_6$, $R_6'$, $R_7$, $R_7'$ and $R_8$ are hydrogen and $R_4$ and $R_5'$ are absent.

The following embodiments are more specific embodiments of the preceding two preferred embodiments. In one embodiment, $R_9$ is alkoxy, oxo or hydroxy. In another embodiment, $R_{10}$ is aryl, substituted aryl, heteroaryl or substituted heteroaryl. In still another embodiment, A is carbon, B and C are nitrogen, $R_{11}$ is hydrogen and $R_{12}$ is aryl, substituted aryl, heteroaryl or substituted heteroaryl. In still another embodiment, A is sulfur, B is carbon and C is nitrogen. In still another embodiment, A is carbon, B is oxygen and C is nitrogen. In still another embodiment, A is carbon, B is nitrogen and C is oxygen.

In one preferred embodiment of compounds of structural formula (III), $R_1$, $R_2$, $R_2'$, $R_3$, $R_3'$, $R_5$, $R_6$, $R_6'$, $R_7$, $R_7'$, $R_8$, $R_{13}$ and $R_{13}'$ are hydrogen, alkyl or arylalkyl and $R_4$ and $R_5'$ are absent. In another preferred embodiment, $R_1$ is methyl, $R_2$, $R_2'$, $R_3$, $R_3'$, $R_5$, $R_6$, $R_6'$, $R_7$, $R_7'$, $R_8$, $R_{13}$ and $R_{13}'$ are hydrogen and $R_4$ and $R_5'$ are absent.

The following embodiments are more specific embodiments of the preceding two preferred embodiments. In one embodiment, $R_9$ is alkoxy, oxo or hydroxy. In another embodiment, $R_{10}$ is aryl, substituted aryl, heteroaryl or substituted heteroaryl. In still another embodiment, A is carbon, B and C are nitrogen, $R_{11}$ is hydrogen and $R_{12}$ is aryl, substituted aryl, heteroaryl or substituted heteroaryl. In still another embodiment, A is sulfur, B is carbon and C is nitrogen. In still another embodiment, A is carbon, B is oxygen and C is nitrogen. In still another embodiment, A is carbon, B is nitrogen and C is oxygen.

In a preferred embodiment of compounds of structural formula (I), $R_1$ is methyl, $R_2$, $R_2'$, $R_3$, $R_3'$, $R_5$, $R_6$, $R_6'$, $R_7$, $R_7'$ and $R_8$ are hydrogen, $R_4$ and $R_5'$ are absent, $R_9$ is alkoxy, oxo or hydroxy, $R_{10}$ is aryl, substituted aryl, heteroaryl or substituted heteroaryl, A is carbon, B and C are nitrogen, $R_{11}$ is hydrogen and $R_{12}$ is aryl, substituted aryl, heteroaryl or substituted heteroaryl. Preferably, $R_9$ is hydroxy and $R_{10}$ is

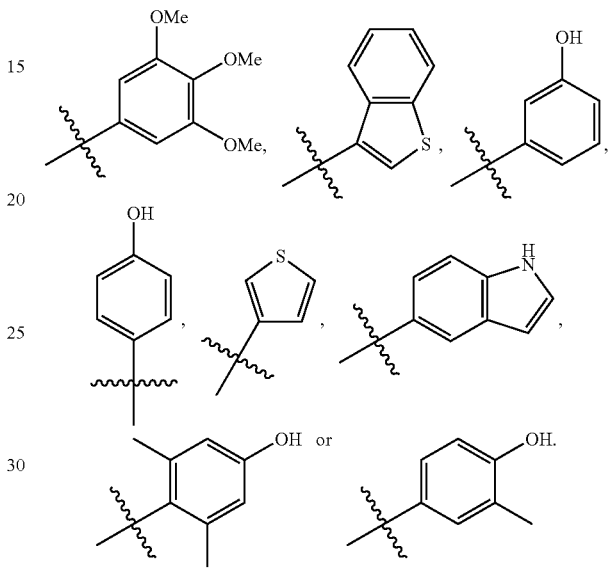

In a preferred embodiment of compounds of structural formula (II), $R_1$ is methyl, $R_2$, $R_2'$, $R_5$, $R_6$, $R_6'$, $R_7$, $R_7'$ and $R_8$ are hydrogen, $R_4$ and $R_5'$ are absent, $R_9$ is alkoxy, oxo or hydroxy, $R_{10}$ is aryl, substituted aryl, heteroaryl or substituted heteroaryl, A is carbon, B and C are nitrogen, $R_{11}$ is hydrogen and $R_{12}$ is aryl, substituted aryl, heteroaryl or substituted heteroaryl.

In a preferred embodiment of compounds of structural formula (III), $R_1$ is methyl, $R_2$, $R_2'$, $R_5$, $R_6$, $R_6'$, $R_7$, $R_7'$, $R_8$, $R_{13}$ and $R_{13}'$ are hydrogen, $R_4$ and $R_5'$ are absent, $R_9$ is alkoxy, oxo or hydroxy, $R_{10}$ is aryl, substituted aryl, heteroaryl or substituted heteroaryl, A is carbon, B and C are nitrogen, $R_{11}$ is hydrogen and $R_{12}$ is aryl, substituted aryl, heteroaryl or substituted heteroaryl.

In one embodiment, compounds of structural formulae (I), (II) and (III) do not include any furanyl derivatives (i.e., when one of A, B or C is oxygen, the remaining members of A, B or C are not carbon). In a more specific embodiment, the compounds of structural formulae (I), (II) and (III) do not include compounds where is oxygen and A and B are carbon or where A is oxygen and B and C are carbon.

In one embodiment of the compounds of structural formulae (I), $R_{10}$ and $R_2$ bond directly to one another to form a 5-membered ring, W is nitrogen, $R_9$ is hydrogen, $R_8$ and $R_2'$ are both absent, and a benzene ring is fused to the bond between $R_{10}$ and $R_2$. In a more specific embodiment, the benzene ring is substituted with a halogen, or an alkoxy group.

In another preferred embodiment, the compounds of structural formulae (I), (II) and (III) of do not include any thienyl derivatives (i.e., when one of A, B or C is sulfur, the remaining members of A, B or C are not carbon). In a more specific embodiment, the compounds of structural formulae (I), (II) and (III) do not include compounds where C is sulfur and A and B are carbon. Preferably, in this embodiment, $R_{11}$ and $R_{12}$ are not hydrogen and methyl, respectively.

Synthesis of the Compounds of the Invention

The compounds of the invention may be obtained via the synthetic methods illustrated in Schemes 1-7, as shown in FIGS. 1-7, respectively. Starting materials useful for preparing compounds of the invention and intermediates thereof are commercially available or can be prepared by well-known synthetic methods. Other methods for synthesis of the compounds described herein are either described in the art or will be readily apparent to the skilled artisan in view of general references well-known in the art (see e.g., Green et al., "Protective Groups in Organic Chemistry", (Wiley, $2^{nd}$ ed. 1991); Harrison et al., "Compendium of Synthetic Organic Methods", Vols. 1-8 (John Wiley and Sons, 1971-1996); "Beilstein Handbook of Organic Chemistry", Beilstein Institute of Organic Chemistry, Frankfurt, Germany; Feiser et al., "Reagents for Organic Synthesis", Volumes 1-17, Wiley Interscience; Trost et al., "Comprehensive Organic Synthesis", Pergamon Press, 1991; "Theilheimer's Synthetic Methods of Organic Chemistry", Volumes 145, Karger, 1991; March, "Advanced Organic Chemistry", Wiley Interscience, 1991; Larock "Comprehensive Organic Transformations", VCH Publishers, 1989; Paquette, "Encyclopedia of Reagents for Organic Synthesis", John Wiley & Sons, 1995) and may be used to synthesize the compounds of the invention. Further, specific references for synthesizing indans, decalins and guanines are easily accessible to the ordinarily skilled artisan. Accordingly, the methods presented in the Schemes herein are illustrative rather than comprehensive.

Compounds depicted in Schemes 1-7 of FIGS. 1-7 are compounds of structural formula (I), or precursors thereof. Those of ordinary skill in the art will appreciate that the synthetic steps illustrated in Schemes 1-7 are also applicable to the preparation of compounds of structural formulae (II) and (In).

A preferred synthetic route to the compounds of structural formula (I) (and, by analogy, to compounds of structural formulae (I) or (II)) proceeds through ketone 107 and/or its derivatives, which may be made by the route depicted in Scheme 1, as depicted in FIG. 1. Six membered dione 101 is either commercially available or may be synthesized from readily available starting materials (the same is true for the five-membered and seven membered analogues of dione 101). Treatment of dione 101 with base and alkylating agent ($R_1$) provides alkylated dione 103, which may be annelated (e.g., using a methyl vinyl ketone equivalent and base) to yield 3-keto decalin 105. Other methods of annelating a six-membered ring are well known to the skilled artisan, (see e.g., Jung, *Tetrahedron*, 32(1), 3-31, (1976)). The unsaturated ketone 105 may be selectively protected with ethanedithiol and acid to yield the unsaturated thioketal 107.

Figure 2:
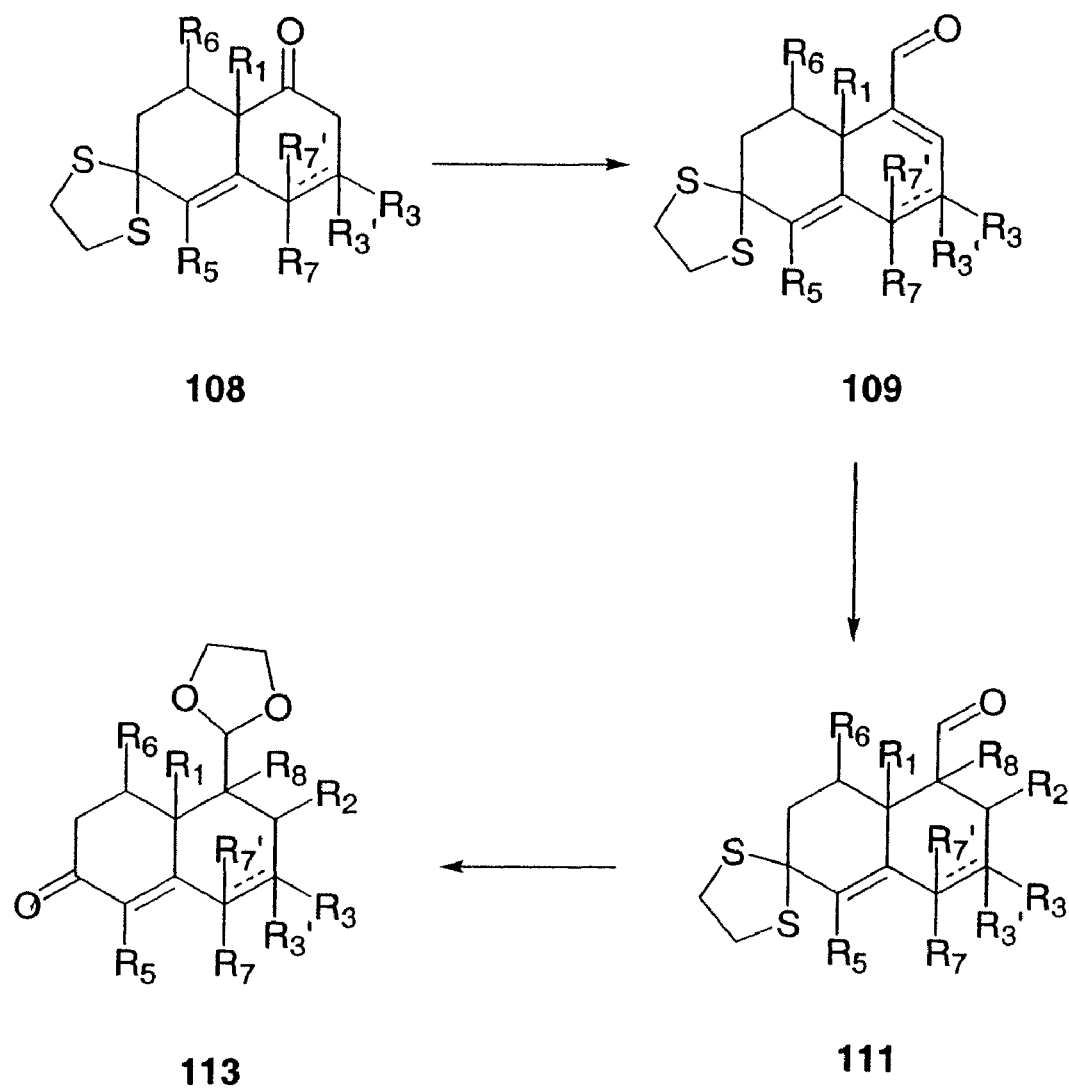
FIG. 2 shows synthesis Scheme 2 for derivatizing an intermediate shown in Scheme 1.

An exemplary method for converting a derivative of 107, thioketal 108 (108 is an embodiment of 107 wherein $R_2$ and $R_2'$ are hydrogen) to ketal 113 is illustrated in Scheme 2, as depicted in FIG. 2. Conversion of 107 to enal 109 may be accomplished by forming an intermediate enol ether (e.g., using a base, such as $Ph_3PCH_2OCH_3$) followed by concurrent dehydrogenation and hydrolysis (e.g., $Pd(OAc)_2$), (see Takayama et al., *J. Org. Chem.*, 1992, 57, 2173). Conjugate addition (e.g., using $(R_2)_2CuLi$), (Coates et al., *J. Org. Chem.*, 39, 275, (1974); Posner et al., *Tet. Lett.*, 3215, (1977)) followed by enolate trapping with $R_8X$ provides aldehyde 111, which may be converted to ketal 113 by a series of conventional reactions (e.g., formation of a ketal and removal of the thioketal).

Figure 3:
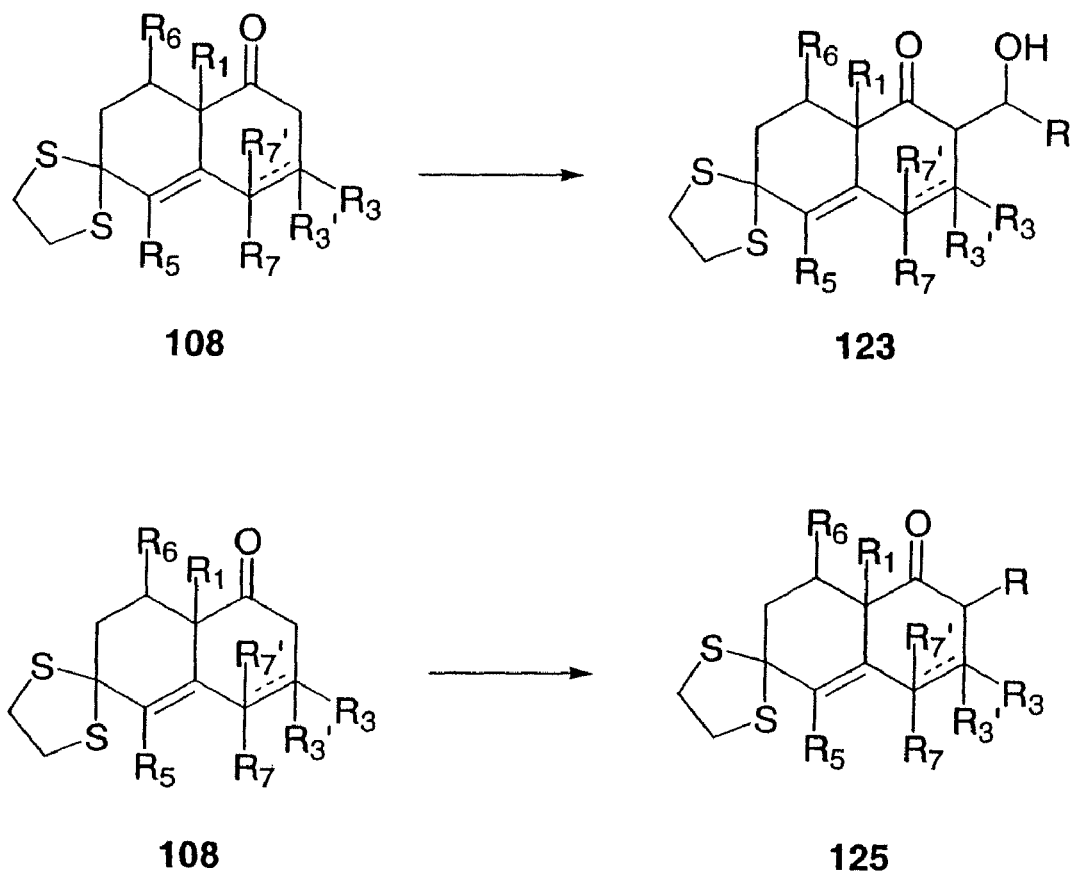
FIG. 3 shows synthesis Scheme 3 for derivatizing a compound shown in Scheme 2.

Alternatively, ketone 108 may be functionalized by well-known methods such as aldol condensation to provide β hydroxy alcohol 123, as illustrated in Scheme 3, depicted in FIG. 3. Ketone 108 may also be alkylated using conventional methods known in the art to provide alkyl derivative 125. It should be noted that when $R_1$, $R_3$, $R_3'$, $R_5$, $R_6$, $R_7$ and $R_7'$ are hydrogen, the compounds where R is n-butyl, benzyl and isobutenyl have been synthesized. Further, other transformations of ketone 108 will be obvious to one of ordinary skill in the art and are within the purview of the present invention (e.g., dehydrogenation to the enone followed by conjugate addition and enolate trapping with an electrophile, γ-alkylation of the enone, dialkylation of the ketone, etc.).

Figure 4:
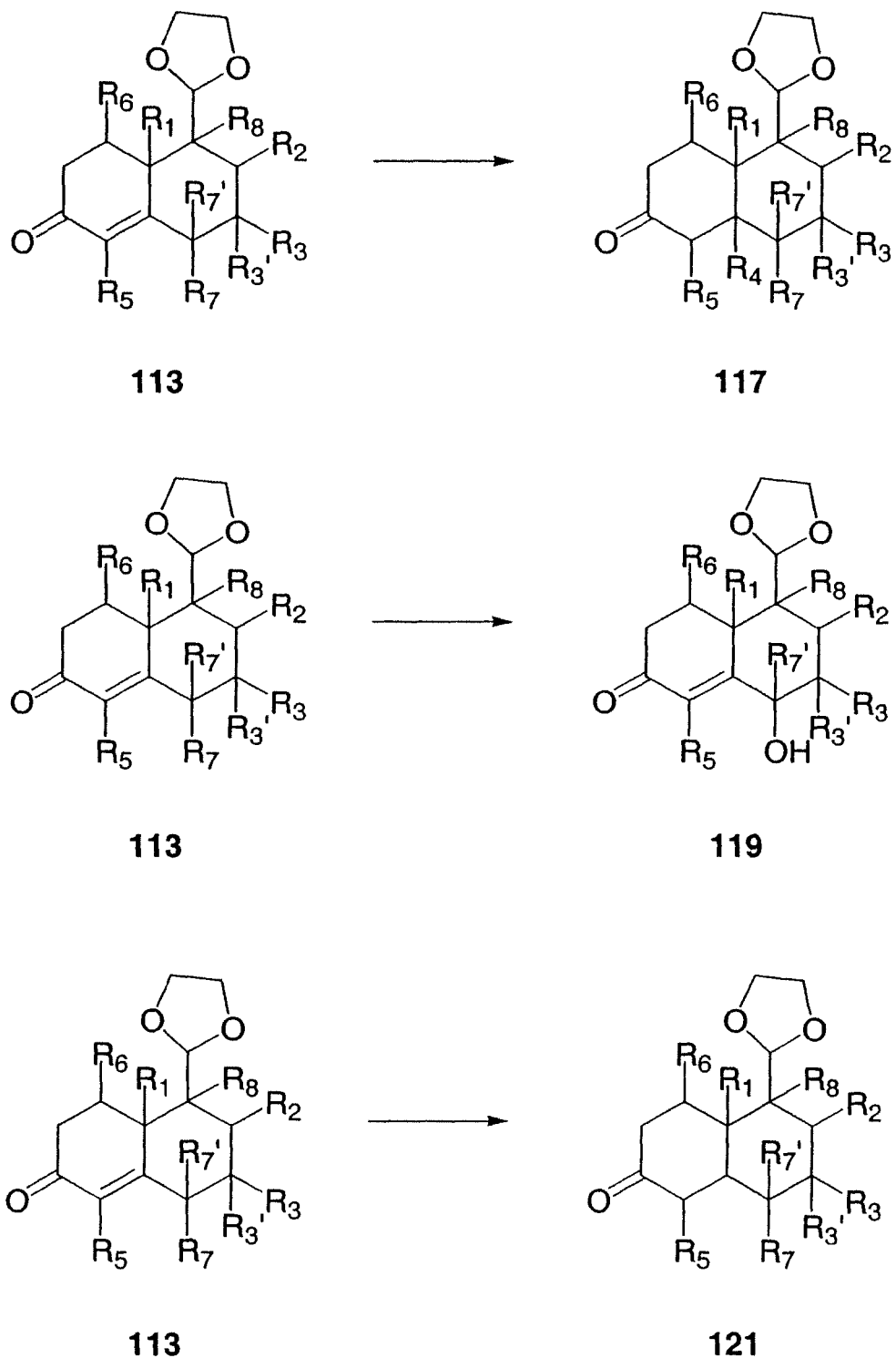
FIG. 4 shows synthesis Scheme 4 for derivatizing a compound shown in Scheme 2.

Ketal-enone 113 may be converted to a number of useful intermediates as illustrated in Scheme 4, as shown in FIG. 4. For example, conjugate addition may be used to provide an $R_4$ substituent (e.g., $(R_4)_2CuLi$ or $R'\equiv$, hydroziroconocene-Cl, MeLi, CuCN, LiCl), (Coates et al., *J. Org. Chem.*, 39, 275, (1974); Posner et al., *Tet. Let.*, 3215, (1977); Lipshutz et al., *J. Am. Chem. Soc.*, 112(20), 7440, (1990)) as in compound 117. Alternatively, 113 may be converted to the γ unsaturated alcohol 119 by treatment, for example, with oxygen, triethylamine and triethylamine oxide (Shimizu et al., *Chem. Pharm. Bull.*, 37(7), 1963, (1989)). The double bond of enone 113 may be hydrogenated (e.g., $H_2$, noble metal catalyst or CuI, LiCl, followed by tri-n-butyl tin hydride) to provide the saturated ketone 221 (Lipshutz et al., *Synlett.*, 64, (1989)). Other transformations of enone 113 will be readily apparent to the artisan of ordinary skill.

Figure 5:
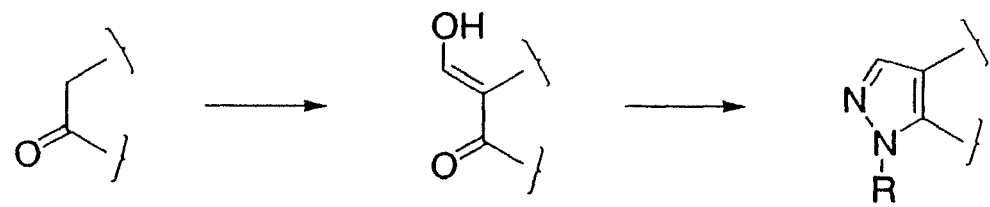
FIG. 5 shows synthesis Scheme 5 for derivatizing a number of ketone moieties.
Figure 5:
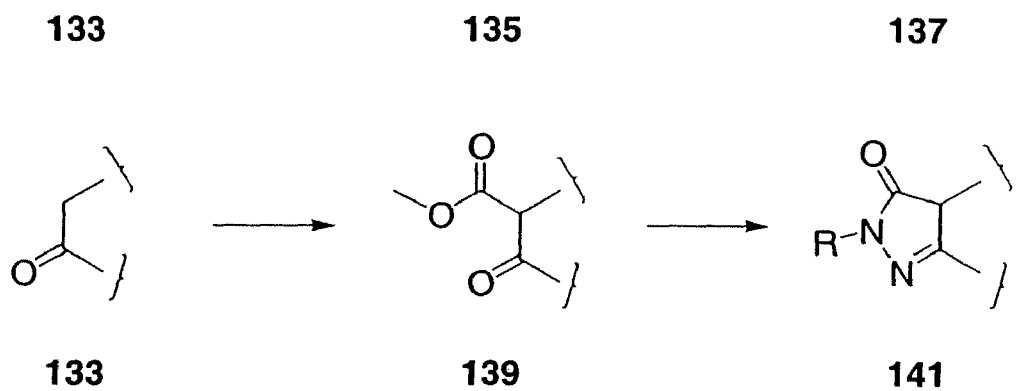
Figure 5:
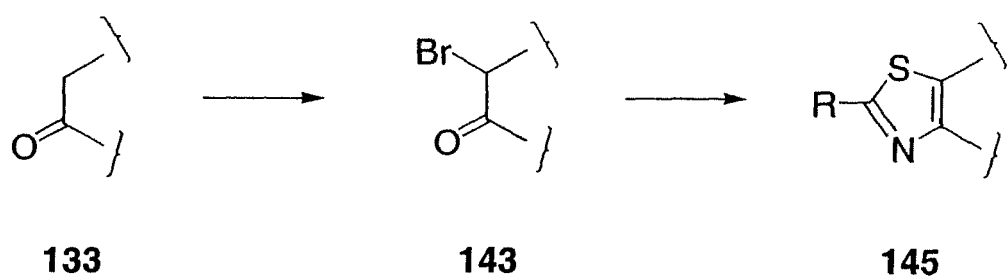
Figure 5:
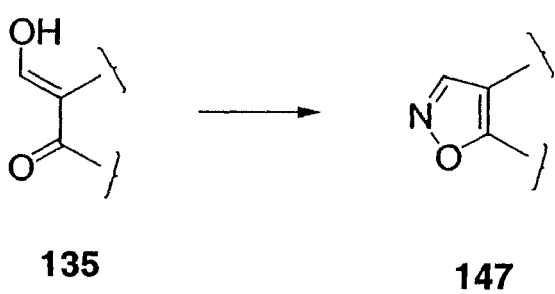
Figure 5:
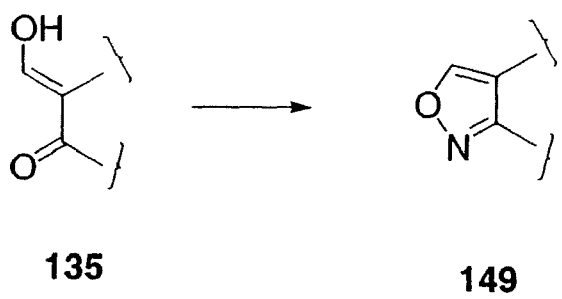

Compounds such as 113 or 121 with a free 3-keto group may be converted to $ heterocyclic compounds by the methods illustrated in Scheme 5, as shown in FIG. 5 (Hashem et al., *J. Med. Chem.*, 19, 229, (1976); Kumar et al., *J. Med. Chem.*, 36, 3278, (1993)). Ketone 133 may be converted to enol ether 135 (e.g., using methyl formate, sodium methoxide, THF) which may be transformed to pyrazole 137 (using e.g., R—NH—$NH_2$, acetic acid or methanol). Ketone 133 may also be converted to β-keto ester 139 (using e.g., diethylcarbonate, sodium methoxide, methyl iodide) which then can be reacted with a hydrazine derivative (i.e., R—NH—$NH_2$) to provide pyrazolone 141. Bromination of ketone 133 (e.g., bromine, chloroform) yields α-bromoketone 143, which upon reaction with a thioamide (i.e., $RCS(NH_2)$) provides thiazole 145. Intermediate enol ether 135 upon reaction with hydroxylamine in the presence of acetic acid and sodium acetate is converted to oxazole 147. Isomeric oxazole 149 is produced when enol ether 135 is reacted with hydroxylamine under basic conditions.

Figure 6:
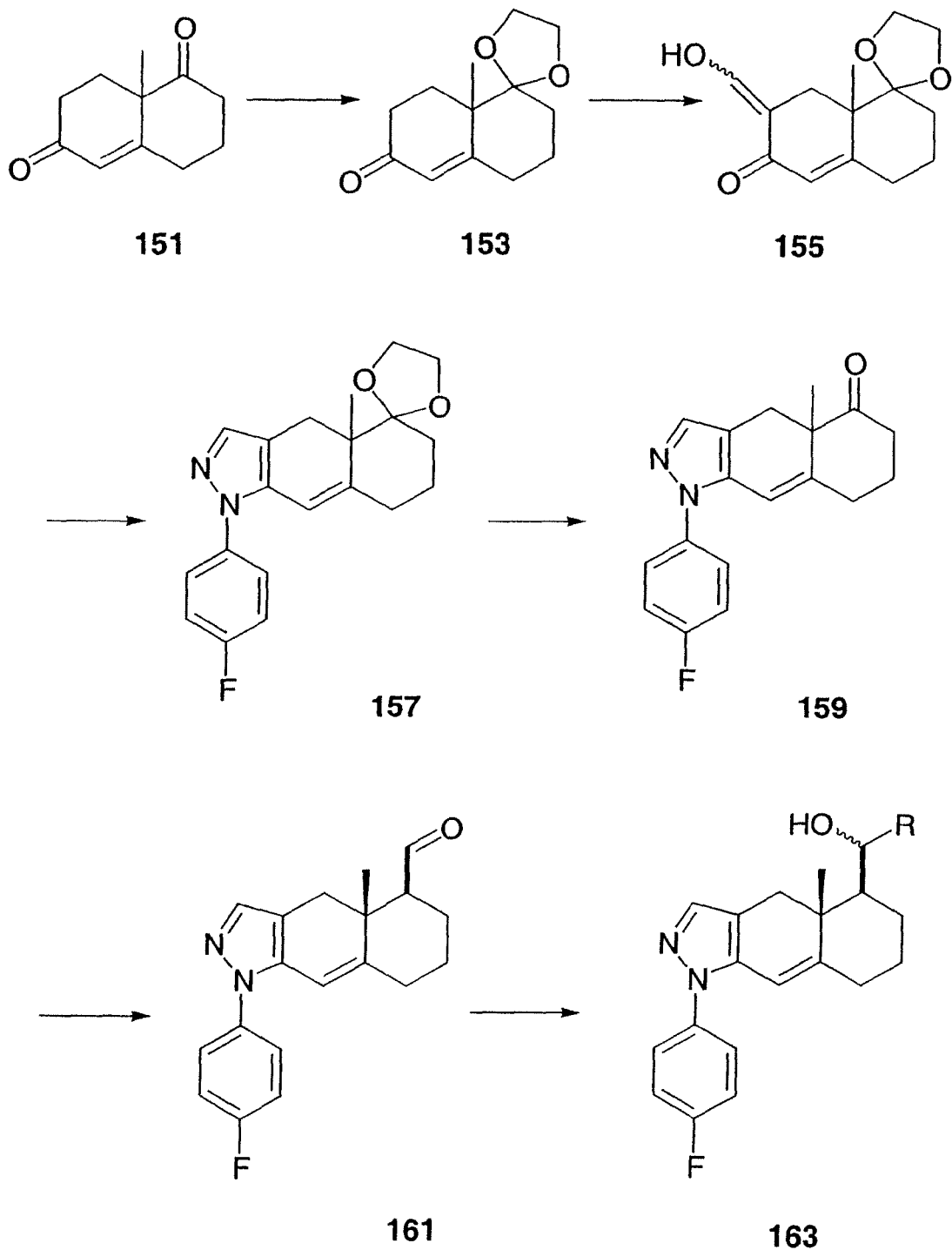
FIG. 6 shows synthesis Scheme 6 for synthesizing compounds of the present invention.

Scheme 6, depicted in FIG. 6, illustrates one possible synthetic route which may be used to prepare compounds of the invention. Wieland-Miescher ketone 151 may be treated with 2-methyl-2-ethyl-1,3 dioxolane ethylene glycol and p-toluenesulfonic acid to provide ketal 153, which may be formylated (using, e.g., sodium methoxide, methyl formate) to give enol 155. Enol 155 may be reacted with p-fluorophenylhydrazine in the presence of sodium acetate provide the p-fluorophenyl pyrazole 157 which then may be deprotected (using, e.g., HCl, methanol, T) to provide ketone 159. Ketone 159 may be converted to aldehyde 161 by Wittig reaction (using, e.g., potassium hexamethyl disilazide, (methoxymethyl) triphenylphosphonium chloride) and hydrolysis of the intermediate enol ether (e.g., HCl). Nucleophilic addition of organolithium reagents to the aldehyde functionality may then provide alcohol 163.

Preferably, R is

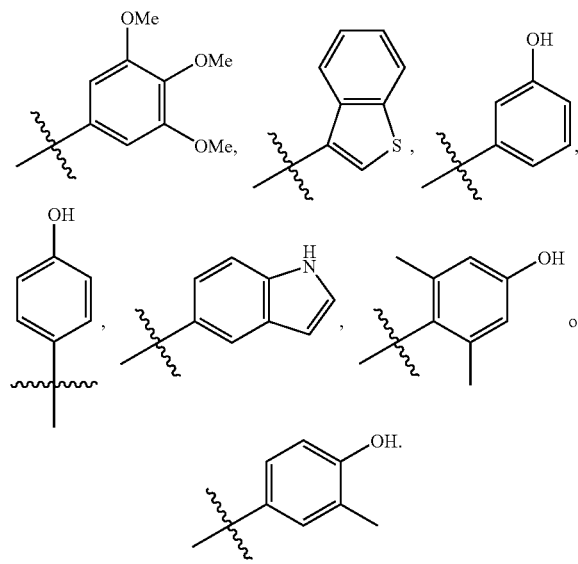

Figure 7:
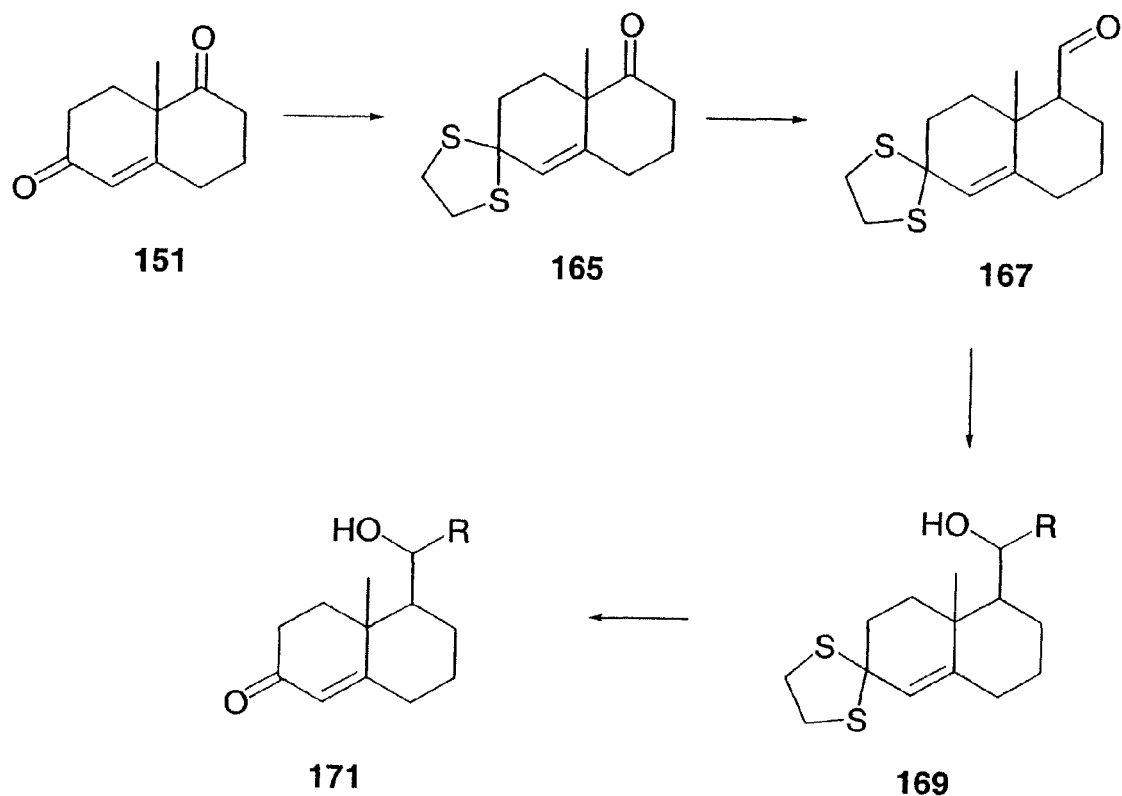
FIG. 7 shows synthesis Scheme 7 for synthesizing compounds of the present invention.

Illustrated in Scheme 7, depicted in FIG. 7, is a synthetic pathway which may be used to prepare some non-pyrazole compounds. Wieland-Miescher ketone 151 may be converted to thioketal 165 (e.g., ethanedithiol, p-toluenesulfonic acid, acetic acid) which can provide aldehyde 167 through Wittig reaction (e.g., potassium hexamethyl disilazide, (methoxymethyl) triphenylphosphonium chloride) and hydrolysis of the intermediate enol ether (e.g., HCl).

Addition of organolithium reagents to aldehyde 167 may be used to provide alcohol 169, which may be deprotected (e.g., $HgClO_4$, methanol/chloroform) to provide enone 171.

Preferably, R is

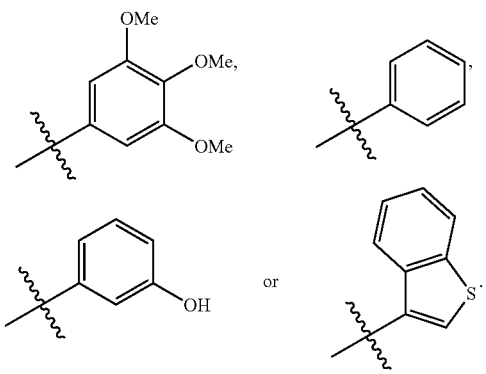

Those of ordinary skill in the art will recognize that enone 171 may be converted to compounds such as 163 illustrated in Scheme 6 through applications of the methods shown in Scheme 5.

Therapeutic Uses of the Compounds of the Invention

The compounds and/or compositions of the present invention may be used to treat diseases associated with either an excess or a deficiency of glucocorticoids in an organism (see e.g., Dowel al., International Publication No. WO 00/66522; Coghlan et al., International Publication No. WO 99/41257; Coghlan et al., International Publication No. WO 99/41256; Coghlan et al., International Publication No. WO 00/06317 WO 00/06137; Jones et al., International Publication No. WO 96/19458).

In accordance with the present invention, a compound and/or composition of the invention is administered to a patient, preferably a human, suffering from diseases, mediated by the glucocorticoid receptor, which include but are not limited to, obesity, diabetes, depression, neurodegeneration or an inflammatory disease. Further, in certain embodiments, the compounds and/or compositions of the invention are administered to a patient, preferably a human, as a preventative measure against various diseases or disorders (see e.g., International Publication No. WO 00/66522, WO 99/41251, WO 00/06137, WO 96/19456). Thus, the compounds and/or compositions of the invention may be administered as a preventative measure to a patient having a predisposition which includes, but is not limited to, obesity, diabetes, depression, neurodegeneration or an inflammatory disease. Accordingly, the compounds and/or compositions of the invention may be used for the prevention of one disease or disorder and concurrently treating another (e.g., preventing depression and treating diabetes).

Procedures for treating diseases, which include but are not limited to, obesity, diabetes, depression, neurodegeneration or an inflammatory disease with prior art compounds have been described in the art (see references above). Thus, those of ordinary skill in the art may readily assay and use the compounds and/or compositions of structural Formulae (I), (II) and (III) to treat diseases, which include but are not limited to, obesity, diabetes, depression, neurodegeneration or an inflammatory disease.

Therapeutic/Prophylactic Administration

The compounds and/or compositions of the invention may be advantageously used in human medicine. As previously described in the preceding section, compounds and compositions of the invention are useful for the treatment or prevention of diseases, which include, but are not limited to, obesity, diabetes, depression, neurodegeneration or an inflammatory disease When used to treat or prevent disease or disorders, compounds and/or compositions of the invention may be administered or applied singly, or in combination with other agents. The compounds and/or compositions of the invention may also be administered or applied singly, or in combination with other pharmaceutically active agents, including other compounds and/or of the invention.

The current invention provides methods of treatment and prophylaxis by administration to a patient of a therapeutically effective amount of a composition and/or compound of the invention. The patient may be an animal, is more preferably a mammal and most preferably a human.

The present compounds and/or compositions of the invention, which comprise one or more compounds of the invention, are preferably administered orally. The compounds and/or compositions of the invention may also be administered by any other convenient route, for example, by infusion or bolus injection, by absorption through epithelial or mucocutaneous linings (e.g., oral mucosa, rectal and intestinal mucosa, etc.). Administration can be systemic or local. Various delivery systems are known, (e.g., encapsulation in liposomes, microparticles, microcapsules, capsules, etc.) that can be used to administer a compound and/or composition of the invention. Methods of administration include, but are not limited to, intradermal, intramuscular, intraperitoneal, intravenous, subcutaneous, intranasal, epidural, oral, sublingual, intranasal, intracerebral, intravaginal, transdermal, rectally, by inhalation, or topically, particularly to the ears, nose, eyes, or skin.

The preferred mode of administration is left to the discretion of the practitioner, and will depend in-part upon the site of the medical condition. In most instances, administration will result in the release of the compounds and/or compositions of the invention into the bloodstream.

In specific embodiments, it may be desirable to administer one or more compounds and/or composition of the invention locally to the area in need of treatment. This may be achieved, for example, and not by way of limitation, by local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. In one embodiment, administration can be by direct injection at the site (or former site) of the disease.

In certain embodiments, it may be desirable to introduce one or more compounds and/or compositions of the invention into the central nervous system by any suitable route, including intraventricular, intrathecal and epidural injection. Intraventricular injection may be facilitated by an intraventricular catheter, for example, attached to a reservoir, such as an Ommaya reservoir.

A compound and/or composition of the invention may also be administered directly to the lung by inhalation. For administration by inhalation, a compound and/or composition of the invention may be conveniently delivered to the lung by a number of different devices. For example, a Metered Dose Inhaler ("MDI"), which utilizes canisters that contain a suitable low boiling propellant, (e.g., dichlorodifluoromethane, trichlorofluoromethane, dichlorotetrafluoroethane, carbon dioxide or any other suitable gas) may be used to deliver compounds of the invention directly to the lung.

Alternatively, a Dry Powder Inhaler ("DPI") device may be used to administer a compound and/or composition of the invention to the lung. DPI devices typically use a mechanism such as a burst of gas to create a cloud of dry powder inside a container, which may then be inhaled by the patient. DPI devices are also well known in the art. A popular variation is the multiple dose DPI ("MDDPI") system, which allows for the delivery of more than one therapeutic dose. For example, capsules and cartridges of gelatin for use in an inhaler or insulator may be formulated containing a powder mix of a compound of the invention and a suitable powder base such as lactose or starch for these systems.

Another type of device that may be used to deliver a compound and/or composition of the invention to the lung is a liquid spray device. Liquid spray systems use extremely small nozzle holes to aerosolize liquid drug formulations that may then be directly inhaled into the lung.

In one embodiment, a nebulizer is used to deliver a compound and/or composition of the invention to the lung. Nebulizers create aerosols from liquid drug formulations by using, for example, ultrasonic energy to form fine particles that may be readily inhaled (see e.g., Verschoyle et al., *British J. Cancer*, 80, Suppl. 2, 96, (1999), which is incorporated herein by reference). Examples of nebulizers include devices supplied by Sheffield/Systemic Pulmonary Delivery Ltd. (see, Armer et al., U.S. Pat. No. 5,954,047; van der Linden er al., U.S. Pat. No. 5,950,619; van der Linden et al., U.S. Pat. No. 5,970,974), Aventis, and Batelle Pulmonary Therapeutics.

In another embodiment, an electrohydrodynamic ("EHD") aerosol device is used to deliver a compound and/or composition of the invention to the lung. EHD aerosol devices use electrical energy to aerosolize liquid drug solutions or suspensions (see e.g., Noakes et al., U.S. Pat. No. 4,765,539). Elm aerosol devices may deliver drugs to the lung more efficiently than other pulmonary delivery technologies.

In another embodiment, the compounds of the invention can be delivered in a vesicle, in particular a liposome (see Langer, *Science*, 249:1527-1533, (1990); Treat et al., in "Liposomes in the Therapy of Infectious Disease and Cancer", Lopez-Berestein and Fidler (eds.), Liss, New York, pp. 353-365, (1989); see generally "Liposomes in the Therapy of Infectious Disease and Cancer", Lopez-Berestein and Fidler (eds.), Liss, New York, (1989)).

In yet another embodiment, the compounds of the invention can be delivered via sustained release systems, preferably oral sustained release systems. In one embodiment, a pump may be used (see Langer, supra; Sefton, *CRC Crit. Ref. Biomed. Eng.*, 14:201, (1987); Saudek et al., *New Engl. J. Med.*, 321:574, (1989)).

In another embodiment, polymeric materials can be used (see "Medical Applications of Controlled Release", Langer and Wise (eds.), CRC Press, Boca Raton, Fla. (1974); "Controlled Drug Bioavailability", Drug Product Design and Performance, Smolen and Ball (eds.), Wiley, New York (1984); Ranger and Peppas, *J. Macromol. Sci. Rev. Macromol. Chem.*, 23:61, (1983); see also Levy et al., *Science*, 228: 190, (1985); During et al., *Ann. Neurol.*, 25:351, (1989); Howard et al, *J. Neurosurg.*, 71:105, (1989)). In a preferred embodiment, polymeric materials are used for oral sustained release delivery. In another embodiment, enteric-coated preparations can be used for oral sustained release administration. In still another embodiment, osmotic delivery systems are used for oral sustained release administration (Verma et al., *Drug Dev. Ind. Pharm.*, 26:695-708, (2000)).

In yet another embodiment, a controlled-release system can be placed in proximity of the target of the compounds and/or composition of the invention, thus requiring only a fraction of the systemic dose (see, e.g., Goodson, in "Medical Applications of Controlled Release", supra, vol. 2, pp. 115-138 (1984)). Other controlled-release systems discussed in Langer, *Science*, 249:1527-1533, (1990), may also be used.

Compositions of the Invention

The present compositions contain a therapeutically effective amount of one or more compounds of the invention, preferably in purified form, together with a suitable amount of a pharmaceutically acceptable vehicle, so as to provide the form for proper administration to a patient. When administered to a patient, the compounds of the invention and pharmaceutically acceptable vehicles are preferably sterile. Water is a preferred vehicle when the compound of the invention is administered intravenously. Saline solutions and aqueous dextrose and glycerol solutions can also be employed as liquid vehicles, particularly for injectable solutions. Suitable pharmaceutical vehicles also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The present compositions, if desired, can also contain minor amounts of wetting or emulsifying agents or pH buffering agents. In addition, auxiliary, stabilizing, thickening, lubricating and coloring agents may be used.

Pharmaceutical compositions comprising a compound of the invention may be manufactured by means of conventional mixing, dissolving, granulating, dragee-making, levigating, emulsifying, encapsulating, entrapping or lyophilizing processes. Pharmaceutical compositions may be formulated in conventional manner using one or more physiologically acceptable carriers, diluents, excipients or auxiliaries, which facilitate processing of compounds of the invention into preparations that may be used pharmaceutically. Proper formulation is dependent upon the route of administration chosen.

The present compositions can take the form of solutions, suspensions, emulsion, tablets, pills, pellets, capsules, capsules containing liquids, powders, sustained-release formulations, suppositories, emulsions, aerosols, sprays, suspensions, or any other form suitable for use. In one embodiment, the pharmaceutically acceptable vehicle is a capsule (see e.g., Grosswald et al., U.S. Pat. No. 5,698,155). Other examples of suitable pharmaceutical vehicles have been described in the art (see Remington's Pharmaceutical Sciences, Philadelphia College of Pharmacy and Science, 17th Edition, 1985).

For topical administration, compounds of the invention may be formulated as solutions, gels, ointments, creams, suspensions, etc., as is well-known in the art.

Systemic formulations include those designed for administration by injection, e.g., subcutaneous, intravenous, intramuscular, intrathecal or intraperitoneal injection, as well as those designed for transdermal, transmucosal, oral or pulmonary administration. Systemic formulations may be made in combination with a further active agent that improves mucociliary clearance of airway mucus or reduces mucous viscosity. These active agents include, but are not limited to, sodium channel blockers, antibiotics, N-acetyl cysteine, homocysteine and phospholipids.

In a preferred embodiment, the compounds of the invention are formulated in accordance with routine procedures as a composition adapted for intravenous administration to human beings. Typically, compounds of the invention for intravenous administration are prepared as solutions in sterile isotonic aqueous buffer. For injection, a compound of the invention may be formulated in aqueous solutions, preferably in physiologically compatible buffers such as Hanks' solution, Ringer's solution, or physiological saline buffer. The solution may contain formulatory agents such as suspending, stabilizing and/or dispersing agents. When necessary, the compositions may also include a solubilizing agent. Compositions for intravenous administration may optionally include a local anesthetic such as lignocaine to ease pain at the site of the injection. Generally, the ingredients are supplied either separately or mixed together in unit dosage form, for example, as a lyophilized powder or water free concentrate in a hermetically sealed container such as an ampoule or sachette indicating the quantity of active agent. When the compound of the invention is administered by infusion, it can be dispensed, for example, with an infusion bottle containing sterile pharmaceutical grade water or saline. When the compound of the invention is administered by injection, an ampoule of sterile water for injection or saline solution can be provided so that the ingredients may be mixed prior to administration.

For transmucosal administration, penetrants appropriate to the barrier to be permeated are used in the formulation. Such penetrants are generally known to one of ordinary skill in the art.

Compositions for oral delivery may be in the form of, for example, tablets, lozenges, aqueous or oily suspensions, granules, powders, emulsions, capsules, syrups, or elixirs. Orally administered compositions may optionally contain one or more agents, for example, sweetening agents such as fructose, aspartame or saccharin; flavoring agents such as peppermint, oil of wintergreen, or cherry coloring agents and preserving agents, to provide a pharmaceutically palatable preparation. Moreover, when in tablet or pill form, the compositions may be coated to delay disintegration and absorption in the gastrointestinal tract, thereby providing a sustained action over an extended period of time. Selectively permeable membranes surrounding an osmotically active driving compound are also suitable for orally administered compounds of the invention. In these latter platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time delay material such as glycerol monostearate or glycerol stearate may also be used. Oral compositions can include standard vehicles such as mannitol, lactose, starch, magnesium stearate, sodium saccharine, cellulose, magnesium carbonate, and the like. Such vehicles are preferably of pharmaceutical grade.

For oral liquid preparations such as, for example, suspensions, elixirs and solutions, suitable carriers, excipients or diluents include water, saline, alkyleneglycols (e.g., propylene glycol), polyalkylene glycols (e.g., polyethylene glycol) oils, alcohols, slightly acidic buffers between pH 4 and pH 6 (e.g., acetate, citrate, ascorbate at between about 5.0 mM to about 50.0 mM, etc). Additionally, flavoring agents, preservatives, coloring agents, bile salts, acylcarnitines and the like may be added.

For buccal administration, the compositions may take the form of tablets, lozenges, etc., formulated in conventional manner.

Liquid drug formulations suitable for use with nebulizers and liquid spray devices and EHD aerosol devices will typically include a compound of the invention with a pharmaceutically acceptable vehicle. Preferably, the pharmaceutically acceptable vehicle is a liquid such as alcohol, water, polyethylene glycol or a perfluorocarbon. Optionally, another material may be added to alter the aerosol properties of the solution or suspension of compounds of the invention. Preferably, this material is liquid such as an alcohol, glycol, polyglycol or a fatty acid. Other methods of formulating liquid drug solutions or suspension suitable for use in aerosol devices are known to those of skill in the alt (see e.g., Biesaiski, U.S. Pat. No. 5,112,598; Biesalski, U.S. Pat. No. 5,556,611).

A compound of the invention may also be formulated in rectal or vaginal compositions such as suppositories or retention enemas, e.g., containing conventional suppository bases such as cocoa butter or other glycerides.

In addition to the formulations described previously, a compound of the invention may also be formulated as a depot preparation. Such long acting formulations may be administered by implantation (for example, subcutaneously or intramuscularly) or by intramuscular injection. Thus, for example, a compound of the invention may be formulated with suitable polymeric or hydrophobic materials (for example, as an emulsion in an acceptable oil) or ion exchange resins, or as sparingly soluble derivatives, for example, as a sparingly soluble salt.

When a compound of the invention is acidic, it may be included in any of the above-described formulations as the free acid, a pharmaceutically acceptable salt, a solvate or hydrate. Pharmaceutically acceptable salts substantially retain the activity of the free acid, may be prepared by reaction with bases and tend to be more soluble in aqueous and other protic solvents than the corresponding free acid form.

Methods of Use and Doses

A compound of the invention and/or compositions thereof, will generally be used in an amount effective to achieve the intended purpose. For use to treat or prevent diseases or disorders such as obesity, diabetes, depression, neurodegeneration or an inflammatory disease, the compounds of the invention and/or compositions thereof, are administered or applied in a therapeutically effective amount.

The amount of a compound of the invention that will be effective in the treatment of a particular disorder or condition disclosed herein will depend on the nature of the disorder or condition and can be determined by standard clinical techniques known in the art as previously described. In addition, in vitro or in vivo assays may optionally be employed to help identify optimal dosage ranges. The amount of a compound of the invention administered will, of course, be dependent on, among other factors, the subject being treated, the weight of the subject, the severity of the affliction, the manner of administration and the judgment of the prescribing physician.

For example, the dosage may be delivered in a pharmaceutical composition by a single administration, by multiple applications or controlled release. In a preferred embodiment, the compounds and/or compositions of the invention are delivered by oral sustained release administration. Preferably, in this embodiment, the compounds and/or compositions of the invention are administered twice per day (more preferably, once per day). Dosing may be repeated intermittently, may be provided alone or in combination with other drugs and may continue as long as required for effective treatment of the disease state or disorder.

Suitable dosage ranges for oral administration are dependent on the potency of the compound of the invention, but are generally about 0.001 mg to about 200 mg of a compound of the invention per kilogram body weight. Dosage ranges may be readily determined by methods known to the skilled artisan.

Suitable dosage ranges for intravenous (i.v.) administration are about 0.01 mg to about 100 mg per kilogram body weight. Suitable dosage ranges for intranasal administration are generally about 0.01 mg/kg body weight to about 1 mg/kg body weight. Suppositories generally contain about 0.01 milligram to about 50 milligrams of a compound of the invention per kilogram body weight and comprise active ingredient in the range of about 0.5% to about 10% by weight. Recommended dosages for intradermal, intramuscular, intraperitoneal, subcutaneous, epidural, sublingual or intracerebral administration are in the range of about 0.001 mg to about 200 mg per kilogram of body weight. Effective doses may be extrapolated from dose-response curves derived from in vitro or animal model test systems. Such animal models and systems are well known in the art.

The compounds of the invention are preferably assayed in vitro and in vivo, for the desired therapeutic or prophylactic activity, prior to use in humans. For example, in vitro assays can be used to determine whether administration of a specific compound of the invention or a combination of compounds of the invention is preferred for reducing convulsion. The compounds of the invention may also be demonstrated to be effective and safe using animal model systems.

Preferably, a therapeutically effective dose of a compound of the invention described herein will provide therapeutic benefit without causing substantial toxicity. Toxicity of compounds of the invention may be determined using standard pharmaceutical procedures and may be readily ascertained by the skilled artisan. The dose ratio between toxic and therapeutic effect is the therapeutic index. A compound of the invention will preferably exhibit particularly high therapeutic indices in treating disease and disorders. The dosage of a compound of the inventions described herein will preferably be within a range of circulating concentrations that include an effective dose with little or no toxicity.

Combination Therapy

In certain embodiments, the compounds of the invention can be used in combination therapy with at least one other therapeutic agent. The compound of the invention and the therapeutic agent can act additively or, more preferably, synergistically. In a preferred embodiment, a compound of the invention is administered concurrently with the administration of another therapeutic agent. In another preferred embodiment, a composition comprising a compound of the invention is administered concurrently with the administration of another therapeutic agent, which can be part of the same composition as the compound of the invention or a different composition. In another embodiment, a composition comprising a compound of the invention is administered prior to or subsequent to, administration of another therapeutic agent. Other therapeutic agents which may be used with the compounds and/or compositions of the invention, include but are not limited to, drugs used to treat nuerodegenerative diseases such as Alzheimer's or Parkinson's disease, anxiety, depression, psychosis, diabetes, obesity, etc. (see, e.g., Dow et al., International Publication No. WO 00/66522).

EXAMPLES

The invention is further defined by reference to the following examples, which describe in detail preparation of compounds and compositions of the invention and assays for using compounds and compositions of the invention. It will be apparent to those of ordinary skill in the art that many modifications, both to materials and methods, may be practiced without departing from the scope of the invention.

All synthetic reactions were performed under an argon atmosphere unless otherwise noted. THF was purified by distillation from sodium benzophenone ketyl before use. All other anhydrous reagents were purchased from Aldrich Chemical Co. Proton and carbon-13 nuclear magnetic resonance spectra ($^1$H NMR, $^{13}$C NMR) were obtained on a Varian INOVA-400 (400 MHz) instrument; $^1$H NMR chemical shifts are reported as δ values in parts per million (ppm) downfield from internal tetramethylsilane; $^{13}$C NMR chemical shifts are reported as δ values with reference to the solvent peak (CDCl$_3$ or DMSO). High resolution mass spectrometry (HR-MS) was performed by the National Bioorganic and Biomedical Mass Spectrometry Resource at the University of California, San Francisco.

Example 1

Preparation of 5,5-(Ethylenedioxy)-4a-methyl-2,3,4,4a,5,6,7,8-octahydronaphtalen-2-one (201)

A mixture of Wieland-Miescher ketone (5.086 g, 28.44 mmol), 2-methyl-2-ethyl-1,3-dioxolane (19.38 mL, 155.0 mmol), ethylene glycol (0.358 mL, 6.43 mmol) and p-toluenesulfonic acid monohydrate (0.4 g, 2.13 mmol) was stirred at room temperature for 30 hours. The reaction was quenched with dropwise addition of triethylamine, diluted with 20 mL of benzene, washed with water, dried over MgSO$_4$, and concentrated under vacuum. The product was triturated from hexanes to yield monoacetal 201 (5.92 g, 94%). $^1$H NMR (CDCl$_3$) δ 1.36 (s, 3H), 1.6-2.0 (m, 5H), 2.2-2.5 (m, 5H), 3.9-4.1 (m, 4H), 5.80 (d, J=Hz, 1H); $^{13}$C NMR (CDCl$_3$)

198.91, 167.55, 125.38, 125.37, 112.12, 65.16, 64.84, 44.81, 33.70, 31.22, 29.81, 26.62, 21.51, 20.27.

Example 2

5,5-(Ethylenedioxy)-3-Hydroxymethylene-4a-methyl-4,4a,5,6,7,8-hexahydro-3H-naphthalen-2-one (203)

A solution of 201 (20 g, 0.090 mmol) in THF (200 mL) was cooled to −5° C. in an ice/methanol bath. NaOMe (19.45 g, 0.360 mol) was added and the mixture stirred for 30 minutes. After slow addition of a cooled solution of methyl formate (55.5 mL, 0.900 mol) in 60 mL THF, the mixture was stirred at room temperature for 24 hours. The mixture was poured into ice-water-HCl (~50 mL conc. HCl in 500 mL $H_2O$), stirred for 5 minutes and then transferred to a separatory funnel. The aqueous layer was extracted with ether (3×100 mL) and the pooled organic extracts were washed with brine, dried ($MgSO_4$), and concentrated. The yellow residue was flash chromatographed (0-50% EtOAc-hexanes) to yield 203 (5.88 g, 26%) as a yellow oil. $^1$H NMR ($CDCl_3$) δ 1.22 (s, 3H), 1.6-1.9 (m, 4H), 2.02 (d, J=14 Hz, 1H), 2.2-2.5 (2H), 2.91 (d, J=14 Hz, 1H), 3.9-4.1 (m, 4H), 5.86 (d, J=2.0 Hz, 1H), 7.37 (s, 1H); $^{13}$C NMR ($CDCl_3$) 188.72, 166.86, 165.35, 165.12, 124.59, 124.25, 111.92, 106.39, 65.33, 65.17, 65.04, 64.89, 46.00, 29.87, 21.33, 20.74, 20.59.

Example 3

1-(4-Fluoro-phenyl)-4a-methyl-1,4,4a,6,7,8-hexahydro-benzo[f]indazol-5-one (205)

In a 250 mL round bottom flask fitted with a Dean-Stark trap and condenser, a mixture of 203 (5.88 g, 23.5 mmol), 4-fluorophenylhydrazine hydrochloride (3.93 g, 24.2 mmol), sodium acetate (1.99 g, 24.2 mmol), and 2 mL glacial acetic acid in 150 mL benzene was heated to reflux for 1 hour. During this time ~1.2 mL of $H_2O$ was collected. Solvents were then evaporated and the dark residue was dissolved in ether, filtered, and concentrated to afford 8.4 g of a dark brown oil.

A mixture of this oil, 1 N HCl (25 in), glacial acetic acid (50 mL) and THF (75 mL) was stirred at room temperature for 48 hours. The reaction was quenched with a saturated $NaHCO_3$ solution. The aqueous layer was extracted with ether (4×50 mL), washed twice with saturated $NaHCO_3$, brine, and then dried ($MgSO_4$), and concentrated. The residue was triturated with boiling hexanes and the combined triturates were recrystallized from EtOH to afford 3.5 g of 205 as an orange powder. Flash chromatography (0-50% EtOAc/hexanes) of the remaining residue afforded an overall yield of 5.67 g (81% over two steps). $^1$H NMR ($CDCl_3$) δ 1.25 (s, 3H), 1.60-1.75 (m, 1H), 2.00-2.15 (m, 1H), 2.5-2.73 (m, 4H), 2.9 (d, J=3 Hz, 2H), 6.29 (d, J=2 Hz, 1H), 7.17 (t, J=8.4 Hz, 2H), 7.43-7.50 (m, 3H); $^{13}$C NMR ($CDCl_3$) 212.57, 162.71, 160.25, 145.79, 138.45, 135.97, 135.75, 135.71, 125.29, 125.21, 116.17, 115.94, 114.11, 110.80, 50.68, 38.55, 31.56, 28.20, 23.30, 22.71; HR-MS calculated for $C_{18}H_{17}FN_2O$: 296.1325, found: 296.1320.

Compound 205 gave an IC50 of 436 nM in a GR binding assay.

Example 4

1-(4-Fluoro-phenyl)-4a-methyl-4,4a,5,6,7,8-hexahydro-1H-benzo[f]indazole-5-carbaldehyde (207)

To a cold (−30° C.) solution of (methoxymethyl)triphenylphosphonium chloride (13.85 g, 40.4 mmol) in THF (40 mL), was added KHMDS (0.5M in toluene, 70.8 mL, 35.4 mmol). The resulting red solution was stirred at 0° C. for 15 minutes before being treated with a solution of 205 (3 g, 10.1 mmol) in THF (40 mL). The mixture was stirred at room temperature for 24 hours. A solution of methanol in THF (1:1, 40 mL) and 4 N HCl (30 mL) was added to the mixture at 0° C. The resulting solution was allowed to stir at room temperature for 26 hours and was them poured into water (30 mL) and extracted with ether (4×50 mL). The combined organic layers were washed with brine, dried ($MgSO_4$), and concentrated. Purification of the residue by flash chromatography on silica gel (0-50% ethyl acetate-hexanes) gave 2.2 g (70%) of 207 as a yellow solid. A small portion was further purified via bisulfite addition for characterization. $^1$H NMR ($CDCl_3$) δ 1.12 (s, 3H), 1.35-1.49 (m, 1H), 1.67-1.8 (m, 1H), 1.87-2.0 (m, 2H), 2.28-2.48 (m, 3H), 2.9 (d, J=16.0 Hz, 1H), 3.1 (d, J=16.0 Hz, 1H), 6.18 (s, 1H), 7.16 (t, J=8.5 Hz, 2H), 7.42-7.48 (m, 3H), 9.90 (d, J=2.0 Hz, 1H); $^{13}$C NMR ($CDCl_3$) 203.99, 162.64, 160.18, 147.26, 137.77, 136.35, 135.65, 135.62, 125.36, 125.32, 125.24, 116.09, 115.87, 113.36, 109.93, 60.78, 39.90, 34.55, 32.10, 24.52, 22.62, 18.96.

Example 5

Preparation of (3-Bromo-phenoxy)-triisopropyl-silane (209)

A mixture of 3-bromophenol (1.00 g, 5.78 mmol), and imidazole (984 mg, 14.45 mmol) in 6 mL of DMF was cooled to 0° C. and triisopropylsilyl chloride (922 μL, 6.94 mmol) was added and the solution was stirred for 24 hours. The reaction mixture was quenched with 10 mL $H_2O$ and 5 mL saturated aqueous $NaHCO_3$. The aqueous layer was extracted with ether (3×10 mL), the pooled organic extracts were washed with brine, dried ($MgSO_4$), and concentrated. The resulting oil was flash chromatographed on silica gel with hexanes to yield 209 (1.50 g, 79%). $^1$H NMR ($CDCl_3$) δ 1.09 (d, J=7.2 Hz, 18H), 1.17-1.30 (m, 3H), 6.75-6.81 (m, 1H), 7.00-7.10 (m, 3H); $^{13}$C NMR ($CDCl_3$) 156.89, 130.26, 124.14, 123.29, 122.5, 118.47.

Example 6

(4-Bromo-3,5-dimethyl-phenoxy)triisopropyl-silane (211)

Following the procedure of Example 5 but substituting 4-bromo-3,5 dimethyl phenol for 3-bromophenol provided 211 in 93% yield. $^1$H NMR ($CDCl_3$) δ 1.22 (d, J=6.0 Hz, 18H), 1.37 (m, 3H), 2.46 (s, 6H), 6.75 (s, 2H); $^{13}$C NMR ($CDCl_3$) 154.54, 138.81, 119.65, 23.85, 17.92, 12.71.

Example 7

(4-Bromo-phenoxy)-triisopropyl-silane (213)

Following the procedure of Example 5 but substituting 4-bromophenol for 3-bromophenol provided 213 in 94% yield. $^1$H NMR ($CDCl_3$) δ 1.09 (d, J=6.8 Hz), 1.23 (quint, J=7.6 Hz, 3H), 6.74 (d, J=8.0 Hz, 2H), 7.28 (d, J=8.0 Hz, 2H); $^{13}$C NMR ($CDCl_3$) 155.17, 132.19, 121.56, 113.24, 17.83, 15.59.

Example 8

(4-Iodo-2-methyl-phenoxy)-triisopropyl-silane (215)

Following the procedure of Example 5 but substituting 4-iodo-2methylphenol for 3-bromophenol provided 215 in 57% yield. $^1$H NMR (CDCl$_3$) δ 1.09 (d, J=8.0 Hz, 18H), 1.26 (sext, J=8.0 Hz, 3H), 2.18 (s, 3H), 6.53 (d, J=8.4 Hz, 1H), 7.30 (d, J=8.4 Hz, 1H), 7.40 (s, 1H); $^{13}$C NMR (CDCl$_3$) 154.23, 139.35, 135.36, 131.38, 119.93, 82.88, 17.97, 17.58, 16.67, 12.93.

Example 9

4-Bromo-2,6-dimethoxy-phenol (217)

To a 500 mL flask fitted with a condenser, 2,6-dimethoxyphenol (10 g, 64.86 mmol) and 80 mL of anhydrous CHCl$_3$ was added. The solution was cooled to −40° C. and NaH (60% dispersion in mineral oil, 26 mg, 0.65 mmol) was added. Another 20 mL of anhydrous CHCl$_3$ was added followed by rapid addition of N-bromo-succinimide (12.77 g, 71.35 mmol). The reaction mixture was stirred for 1 hour at −35° C., heated to room temperature over the next 30 minutes and heated to reflux for another 30 minutes. The solvent was evaporated under vacuum overnight. The tan solid was stirred with 100 mL ether, the mixture was filtered, and the residue was washed with ether. The solvent was evaporated under vacuum to yield a tan solid, which was then dissolved in boiling hexanes. The solution was decanted from the brown oil and filtered through a pre-heated celite pad into a heated flask. The light yellow solution was allowed to cool at room temperature for 3 hours. White wooly needles were filtered off and dried to yield 217 (3.22 g, 22%). $^1$H NMR (CDCl$_3$) δ 6.72 (s, 2H), 5.44 (s, 1H), 3.88 (s, 6H); $^{13}$C NMR (CDCl$_3$) 147.47, 133.93, 110.88, 108.38, 56.33.

Example 10

5-Bromo-1,2,3-trimethoxy-benzene (219)

A mixture of 5-bromo-1,2,3 trihydroxybenzene (1.3 g, 5.63 mmol) and 1M NaOH (14 mL) was cooled to 10° C. and dimethyl sulfate (800 μL, 16.89 mmol) was added. This mixture was heated at reflux for 3 hours and another portion of dimethyl sulfate (800 μL) was added. The mixture was heated at reflux for another 3 hours. The mixture was cooled overnight, and a gray solid was filtered off, which was then dissolved in ~50 mL ether, washed with 5% NaOH—H$_2$O, water (2×), brine, then dried (MgSO$_4$), and concentrated to yield 219 (1.39 g, 76%). $^1$H NMR (CDCl$_3$) δ 6.72 (s, 2H), 3.85 (s, 6H), 3.82 (s, 3H); $^{13}$C NMR (CDCl$_3$) 136.67, 137.11, 115.92, 108.07, 60.58, 56.05.

Example 11

3a,7a-(Dihydro-benzo[b]thiophen-3-yl)-[1-(4-fluoro-phenyl)-4a-methyl-4,4a,5,6,7,8-hexahydro-1H-benzo[f]indazol-5-yl]-methanol (221)

A solution of 3-bromo-benzo[b]thiophene (86.2 μL, 0.659 mmol) in 5 mL anhydrous diethyl ether was cooled to −8° C. and tert-butyl lithium (1.7M in pentane, 775 μL, 1.318 mmol) was added and the mixture was stirred for 15 minutes at −78° C. and then 2 hours at room temperature. Aldehyde 207, dissolved in 10 mL of ether was added dropwise over 10 minutes at −30° C. and the mixture was stirred for 0.5 hours. The reaction was quenched with dropwise addition of saturated aqueous NH$_4$Cl. The aqueous layer was extracted with ether (3×10 mL) and the combined organic extracts were washed with saturated aqueous NaHCO$_3$, brine, dried (MgSO$_4$), and concentrated. The residue was purified by flash chromatography (20% EtOAc-hexanes), followed by preparative TLC (25% EtOAc-hexanes) to yield 221 (18.1 mg, 32%) as a mixture of isomers. Fraction A: $^1$H NMR (CDCl$_3$) δ 1.27 (s, 3H), 1.70-1.92 (m, 3H), 1.97 (m, 1H), 2.25-2.5 (m, 3H), 2.74 (d, J=15.2 Hz, 1H), 3.14 (d, J=15.2 Hz, 1H), 3.41 (d, J=1.6 Hz, 1H), 5.44 (d, J=5.2 Hz, 1H), 6.13 (d, J=2.0 Hz, 1H), 7.16 (t, J=8.4 Hz, 2H), 7.21 (s, 1H), 7.27-7.37 (m, 2H), 7.42-7.50 (m, 3H), 7.72 (d, J=8.0 Hz, 1H), 7.80 (d, J=8.0 Hz, 1H); HR-MS calculated for C$_{27}$H$_{25}$FN$_2$OS: 444.1672, found: 444.1675. Fraction B: $^1$H NMR (CDCl$_3$) δ 1.27 (s, 3H), 1.80-2.10 (m, 4H), 2.20-2.50 (m, 3H), 2.58-2.65 (m, 1H), 3.04 (t, J=15.2 Hz, 1H), 3.19 (d, J=15.2 Hz, 1H), 3.41 (d, J=1.6 Hz, 2H), 3.63 (d, J=4.4 Hz, 1H), 6.12 (s, 1H), 7.11-7.18 (m, 2H), 7.35-7.48 (m, 4H), 7.49 (s, 1H), 7.80 (t, J=5.2 Hz, 2H).

Example 12

[1-(4-Fluoro-phenyl)-4a-methyl-4,4a,5,6,7,8-hexahydro-1H-benzo[f]indazol-5-yl]-(3,4,5-trimethoxyphenyl)-methanol (223)

Following the procedure of Example 11 but substituting 5-bromo-1,2,3-trimethoxy-benzene for 3-bromo-benzo[b]thiophene gave 223. $^1$H NMR (CDCl$_3$) δ 1.26 (s, 3H), 1.60-1.90 (m, 4H), 2.00-2.20 (m, 2H), 2.24-2.47 (m, 2H), 2.73 (d, J=15.2 Hz, 1H), 3.20 (d, J=15.2 Hz, 1H), 3.80-3.90 (m, 9H), 5.10 (s, 1H), 6.12 (s, 1H), 6.50-6.60 (m, 2H), 7.10-7.20 (m, 2H), 7.40-7.50 (m, 2H); $^{13}$C NMR (CDCl$_3$); HR-MS calculated for C$_{28}$H$_{31}$FN$_2$O$_4$: 478.2268, found: 478.2261.

Example 13

4-{[1-(4-Fluoro-phenyl)-4a-methyl-4,4a,5,6,7,8-hexahydro-1H-benzo[f]indazol-5-yl]-hydroxy-methyl}-3,5-dimethyl-phenol (227)

Following the procedure of Example 11, but substituting 4-bromo-3,5-dimethyl-phenoxy)-triisopropylsilane for 3-bromo-benzo[b]thiophene gave the triisopropylsilyl ether of 4-{[1-(4-Fluoro-phenyl)-4a-methyl-4,4a,5,6,7,8-hexahydro-1H-benzo[f]indazol-5-yl]-hydroxy-methyl}-3,5-dimethyl-phenol 225. The silyl ether 225 (118.2 mg, 0.201 mmol) was dissolved in 2.5 mL THF and cooled to −78° C. Tetrabutylammonium fluoride (1M in THF, 273 μL, 0.273 mmol) was added dropwise and the solution stirred for 15 minutes. The reaction was quenched with 5 mL H$_2$O. The aqueous phase was extracted with ether (4×5 mL) and the pooled organic extracts were washed with brine, dried (MgSO$_4$), and concentrated. The residue was purified by flash chromatography over silica gel (0-2% MeOH—CHCl$_3$) and then the off-white solid product was washed with methanol to yield 227 (56 mg, 64%) as a white solid. $^1$H NMR (DMSO) δ 1.20 (s, 3H), 1.50-1.80 (m, 4H), 2.34 (s, 6H), 2.61 (d, J=15.2 Hz, 1H), 2.94 (d, J=15.2 Hz, 1H), 4.0 (s, 2.5H) 5.26 (d, J=2.8 Hz, 1H), 6.15 (s, 1H), 6.38 (s, 2H), 7.32 (t, J=8.8 Hz), 7.43 (s, 1H), 7.51 (t, J=4.8 Hz, 2H); $^{13}$C NMR (DMSO) 161.96, 159.54, 154.92, 151.55, 137.86, 136.32, 135.87, 132.34, 125.24, 125.16, 116.34, 116.11, 113.86, 108.29, 69.66, 52.89, 33.25, 32.55, 25.99, 22.47, 21.79, 19.75.

Example 14

4-{[1-(4-Fluoro-phenyl)-4a-methyl-4,4a,5,6,7,8-hexahydro-1H-benzo[f]indazol-5-yl]-keto-methyl}-3,5-dimethyl-phenol (228)

The triisopropylsilyl ether of 4-{[1-(4-Fluoro-phenyl)-4a-methyl-4,4a,5,6,7,8-hexahydro-1H-benzo[f]indazol-5-yl]- hydroxy-methyl}-3,5-dimethyl-phenol (100 mg, 0.17 mmol) was dissolved in 8 mL $CH_2Cl_2$. Pyridinium chlorochromate (55 mg, 0.255 mmol) was added to the solution, which was stirred for 4.5 hours at room temperature under argon. 20 mL diethyl ether was added to the mixture and volatiles were removed under vacuum. The residue was purified by flash chromatography (10% EtOAc-hexanes) to yield the silyl ether of 1 (58.7 mg, 59%) of a clear oil. This oil (58.7 mg, 0.10 mmol) was dissolved in 6 mL THF and cooled to −78° C. Tetrabutylammonium fluoride (1M in THF, 140 μL, 0.14 mmol) was added dropwise and the solution stirred for 15 minutes. The reaction was quenched with 5 mL $H_2O$. The aqueous phase was extracted with ether (4×5 mL) and the pooled organic extracts were washed with brine, dried ($MgSO_4$), and concentrated. The residue was purified by flash chromatography over silica gel (10-20% ethyl acetate-benzene) to yield 228 (45 mg, 100%). $^1$H NMR ($CDCl_3$) δ 1.31 (s, 3H) 1.41 (m, 1H) 1.87 (m, 3H) 2.23 (s, 6H) 2.31 (d, J=15.14 Hz, 1H) 2.43 (m, 1H) 2.62 (d, J=16.11 Hz, 1H) 3.04 (m, 1H) 3.15 (d, J=15.63 Hz, 1H) 6.12 (s, 1H) 6.44 (s, 2H) 7.14 (t, J=8.55 Hz, 2H) 7.36 (s, 1H) 7.39 (s, 1H) 7.43 (dd, J=8.79, 4.88 Hz, 2H); $^{13}$C NMR ($CDCl_3$) 18.33, 20.48, 25.30, 26.11, 32.48, 33.76, 41.81, 61.53, 109.41, 113.94, 115.36, 116.04, 116.27, 125.57, 125.66, 128.32, 134.57, 135.35, 135.38, 135.91, 136.76, 137.79, 149.43, 156.49, 160.39, 210.97.

Example 15

4-{[1-(4-Fluoro-phenyl)-4a-methyl-4,4a,5,6,7,8-hexahydro-1H-benzo[f]indazol-5-yl]-methyl}-3,5-dimethyl-phenol (230)

The triisopropylsilyl ether of 4-{[1-(4-Fluoro-phenyl)-4a-methyl-4,4a,5,6,7,8-hexahydro-1H-benzo[f]indazol-5-yl]-hydroxy-methyl}-3,5-dimethyl-phenol (20 mg, 0.034 mmol) was dissolved in 3 mL $CH_2Cl_2$ and cooled to −78° C. Triethylsilane (16 μL, 0.102 mmol) and boron trifluoride-etherate (19 μL, 0.153 mmol) were added and the solution was stirred for 6 h at room temperature under an argon atmosphere. The reaction was quenched with 2 mL saturated aqueous sodium bicarbonate and extracted with ether (4×5 mL), dried ($MgSO_4$), and concentrated to yield 23.3 mg of a white solid. The silyl ether of 230 was then deprotected following the procedure of Example 14 to yield 230 (16.2 mg, 95%). $^1$H NMR ($CDCl_3$) δ 1.04 (s, 3H) 1.10 (d, J=12.70 Hz, 1H) 1.16 (m, 1H) 1.30 (m, 2H) 1.67 (m, 2H) 2.21 (d, J=5.37 Hz, 6H) 2.29 (m, 2H) 2.48 (m, 1H) 2.70 (m, 2H) 3.07 (d, J=15.14 Hz, 1H) 4.94 (s, 1H) 6.06 (d, J=1.95 Hz, 1H) 6.44 (s, 2H) 7.08 (t, J=8.55 Hz, 2H) 7.39 (m, 3H); $^{13}$C NMR ($CDCl_3$) 12.29, 12.70, 17.42, 17.70, 17.98, 20.90, 26.23, 26.66, 28.61, 33.39, 33.80, 41.63, 48.96, 109.19, 114.09, 115.11, 115.94, 116.16, 125.40, 125.48, 128.32, 129.57, 135.76, 137.01, 137.93, 138.24, 138.37, 150.74, 153.41, 160.26, 162.71.

Example 16

4-{[1-(4-Fluoro-phenyl)-4a-methyl-4,4a,5,6,7,8-hexahydro-1H-benzo[f]indazol-5-yl]-methoxymethoxy-methyl}-3,5-dimethyl-phenol (232)

The triisopropylsilyl ether of 4-{[1-(4-Fluoro-phenyl)-4a-methyl-4,4a,5,6,7,8-hexahydro-1H-benzo[f]indazol-5-yl]-hydroxy-methyl}-3,5-dimethyl-phenol (50 mg, 0.085 mmol) was dissolved in 10 mL $CH_2Cl_2$. Diisopropylethylamine (222 μL, 1.275 mmol) and methoxylmethyl chloride (65 μL, 0.850 mmol) were added and the solution was stirred at room temperature for 10 h. The mixture was diluted with 30 mL ethyl acetate. The organic phase was washed with brine, dried ($Na_2SO_4$), and concentrated to yield 96.3 mg of the silyl ether of 232. This was then deprotected following the procedure of Example 14 to yield 232 (12.4 mg, 59%). $^1$H NMR ($CDCl_3$) δ 1.20 (s, 3H) 1.29 (m, 2H) 1.63 (m, 2H) 1.89 (d, J=13.18 Hz, 1H) 2.14 (m, 2H) 2.28 (d, J=14.65 Hz, 1H) 2.36 (s, 3H) 2.39 (s, 3H) 2.55 (m, 1H) 3.39 (s, 2H) 4.43 (s, 2H) 5.11 (d, J=6.35 Hz, 1H) 6.08 (s, 1H) 6.31 (m, 1H) 6.47 (s, 2H) 7.13 (t, J=7.81 Hz, 2H) 7.36 (d, J=1.95 Hz, 2H) 7.43 (dd, J=6.84, 4.88 Hz, 2H); $^{13}$C NMR ($CDCl_3$) 19.30, 21.22, 21.58, 24.29, 26.24, 33.23, 33.33, 42.16, 52.01, 56.32, 74.08, 93.81, 108.73, 114.12, 115.40, 115.96, 116.19, 117.31, 125.35, 125.43, 128.33, 129.41, 135.62, 135.65, 136.78, 137.88, 138.41, 139.84, 151.68, 154.70, 160.25, 162.71.

Example 17

Binding Data for Compounds 227, 228, 230 and 232

Representative results of glucocorticoid receptor (OR) binding data for 4-{[1-(4-Fluoro-phenyl)-4a-methyl-4,4a,5,6,7,8-hexahydro-1H-benzo[f]indazol-5-yl]-methyl}-3,5-dimethyl-phenol and certain derivatives are shown in Table 1, compared to dexamethasone.

TABLE 1

| Compound | GR Binding RBA (dexamethasone = 100) | GR pot(EC50, nM) |
|---|---|---|
| 227 | 50 | 125 |
| 228 | 16 | — |
| 230 | 22 | — |
| 232 | 26 | 82 |
| dexamethasone | 100 | 2.2 ± 0.1 |

Example 18

3-{[1-(4-Fluoro-phenyl)-4a-methyl-4,4a,5,6,7,8-hexahydro-1H-benzo[f]indazol-5-yl]-hydroxy-methyl}-phenol (229)

Following the procedure of Example 11 but substituting 3-bromo-phenoxy-triisopropylsilane for 3-bromo-benzo[b]thiophene gave the triisopropylsilyl ether of 3-{[1-(4-Fluoro-phenyl)-4a-methyl-4,4a,5,6,7,8-hexahydro-1H-benzo[f]indazol-5-yl]-hydroxy-methyl}-phenol 229, which was then deprotected following the procedure of Example 13. $^1$H NMR ($CDCl_3$) δ 1.14 (s, 5H), 1.18-1.30 (m, 7H), 1.36 (s, 1H), 1.5-1.7 (m, 5H), 1.8-1.95 (m, 2H), 2.20-2.32 (m, 3H), 2.60 (d, J=15.9 Hz, 0.5H), 2.71 (d, J=15.4 Hz, 0.5H), 2.78 (d, J=16.2 Hz, 1H), 2.98 (s, 1H), 3.17 (t, J=15.6 Hz, 1H), 3.65 (d, J=16.2 Hz, 1H), 4.56 (d, J=8.9 Hz, 1H), 4.99 (s, 0.5H), 5.09 (s, 0.5H), 6.09 (s, 0.3H), 6.11 (s, 0.3H), 6.13 (s, 1H), 6.15 (s, 0.4H), 6.7-6.9 (m, 6H), 7.1-7.22 (m, 5H), 7.4-7.5 (m, 5H); $^{13}$C NMR ($CDCl_3$) 162.68, 160.22, 156.34, 155.97, 151.06, 147.46, 146.72, 138.20, 137.89, 137.44, 136.78, 135.61, 129.68, 129.58, 129.48, 125.38, 125.30, 125.26, 125.18, 119.34, 117.67, 116.30, 116.16, 115.93, 115.45, 115.04, 114.72, 114.05, 113.73, 112.72, 109.53, 109.46, 72.40, 71.91, 65.86, 56.53, 53.94, 50.70, 49.39, 41.52, 41.46, 41.29, 40.89, 35.79, 33.83, 30.30, 28.70, 27.57, 27.07, 25.34, 25.16, 23.59, 22.64, 21.33, 20.58, 17.84, 17.67, 15.22.

Example 19

4-{[1-(4-Fluoro-phenyl)-4a-methyl-4,4a,5,6,7,8-hexahydro-1H-benzo[f]indazol-5-yl]-hydroxy-methyl}-phenol (231)

Following the procedure of Example 11 but substituting 4-bromo-phenoxy)-triisopropylsilane for 3-bromo-benzo[b]thiophene gave the triisopropylsilyl ether of 4-{[1-(4-fluoro-phenyl)-4a-methyl-4,4a,5,6,7,8-hexahydro-1H-benzo[f]indazol-5-yl]-hydroxy-methyl}-phenol 231 which was then deprotected following the procedure of Example 13. $^1$H NMR (MeOD) δ 1.00-1.13 (m, 12H), 1.24 (s, 3H), 1.26-1.40 (m, 3H), 1.55-2.00 (m, 7H), 2.25-2.50 (m, 4H), 2.65-2.80 (m, 2H), 3.20 (d, J=15.9 Hz, 1H), 3.65 (d, J=15.9 Hz, 1H), 5.07 (s, 1H), 5.48 (s, 0.5H), 6.07-6.17 (m, 1.5H), 6.71-6.80 (m, 2H), 7.17 (j, J=8.6 Hz, 3H), 7.26 (t, J=8.6 Hz, 3H), 7.39-7.49 (m, 4H); $^{13}$C NMR (CDCl$_3$) 162.66, 160.20, 150.74, 149.99, 149.94, 144.08, 143-27, 138.26, 138.03, 137.99, 137.17, 136.71, 136.43, 135.82, 130.10, 129.97, 129.49, 125.66, 125.37, 125.29, 125.23, 125.14, 124.40, 124.33, 116.13, 116.09, 115.89, 115.87, 115.22, 114.65, 114.04, 109.83, 109.62, 109.28, 105.72, 105.42, 71.22, 69.29, 56.86, 55.24, 53.84, 48.85, 41.60, 41.58, 41.20, 35.71, 34.67, 33.69, 33.36, 27.69, 25.96, 25.63, 25.32, 23.74, 21.43, 20.58, 20.02, 18.09, 17.77.

Example 20

4-{[1-(4-Fluoro-phenyl)-4a-methyl-4,4a,5,6,7,8-hexahydro-1H-benzo[f]indazol-5-yl]-hydroxy-methyl}-2-methyl-phenol (235)

Following the procedure of Example 11 but substituting (4-bromo-2-methyl-phenoxy)-triisopropylsilane for 3-bromo-benzo[b]thiophene gave the triisopropylsilyl ether of 4-{[1-(4-Fluoro-phenyl)-4a-methyl-4,4a,5,6,7,8-hexahydro-1H-benzo[f]indazol-5-yl]-hydroxy-methyl}-2-methyl-phenol 233 which was then deprotected following the procedure of Example 13 to provide 235 in 25% yield. $^1$H NMR (CDCl$_3$) δ 1.25 (3H), 1.50-1.80 (m, 6H), 2.26 (s, 3H), 2.27-2.47 (m, 2H), 2.73 (d, J=15.2 Hz, 1H), 3.16 (d, J=15.2 Hz, 1H), 5.10 (s, 1H), 6.10 (s, 1H), 6.73 (d, J=8.4 Hz, 1H), 7.03 (d, J=8.4 Hz, 1H), 7.07 (s, 1H), 7.14 (t, J=8.0 Hz, 2H), 7.40-7.50 (m, 3H). $^{13}$C NMR (CDCl$_3$) 158.97, 149.16, 146.84, 134.20, 133.86, 124.28, 121.70, 121.62, 120.18, 119.94, 112.41, 112.18, 110.88, 110.17, 105.31, 68.02, 52.95, 47.28, 37.53, 31.34, 29.64, 27.18, 22.04, 16.24, 16.15, 12.22.

Example 21

[1-(4-Fluoro-phenyl)-4a-methyl-4,4a,5,6,7,8-hexahydro-1H-benzo[f]indazol-5-yl]-(1H-indol-4-yl)-methanol (14%) (237)

Following the procedure of Example 11 but substituting 5-bromoindole for 3-bromo-benzo[b]thiophene gave (237) in 14% yield. $^1$H NMR (CDCl$_3$) δ 1.26 (s, 3H), 1.50-1.80 (m, 4H), 2.10-2.50 (m, 3H), 2.77 (d, J=15.2 Hz, 1H), 3.16 (d, J=15.2 Hz, 1H), 5.24 (d, J=2.4 Hz, 1H), 6.08 (d, J=2.0 Hz, 1H), 6.53 (s, 1H), 7.14-7.22 (m, 4H), 7.32 (d, J=8.4 Hz, 1H), 7.40-7.50 (m, 3H), 7.64 (s, 1H), 8.52 (s, 1H); $^{13}$C NMR (CDCl$_3$) 150.82, 137.92, 137.21, 136.94, 134.86, 127.61, 125.34, 125.26, 124.73, 119.87, 117.04, 116.07, 115.84, 115.80, 114.01, 110.76, 108.87, 102.41, 72.33, 60.37, 56.90, 41.29, 34.97, 33.89, 25.77, 19.94, 19.79, 14.13.

Example 22

[1-(4-Fluoro-phenyl)-4a-methyl-4,4a-5,6,7,8-hexahydro-1H-benzo[f]indazol-5-yl]-thiophen-3-yl-methanol (238)

Following the procedure of Example 11 but substituting 3-bromothiophene for 3-bromo-benzo[b]thiophene gave (238) in 20% yield as a mixture of isomers. $^1$H NMR (CDCl$_3$) δ 1.22 (s, 3H), 1.70-1.94 (m, 4H), 2.24-2.48 (m, 2H), 2.96 (d, J=15.3 Hz, 1H), 2.99 (s, 1H), 3.13 (d, J=15.3 Hz, 1H), 5.42 (d, J=3.7 Hz, 1H), 6.10 (d, J=2.3 Hz, 1H), 6.93 (d, J=5.2 Hz, 1H), 7.14 (m, 2H), 7.22 (d, J=5.2 Hz, 1H), 7.40-7.46 (m, 3H); $^{13}$C NMR (CDCl$_3$) 150.21, 144.41, 137.94, 136.77, 135.75, 130.04, 125.39, 125.30, 124.25, 116.12, 115.89, 114.03, 109.15, 105.18, 69.09, 53.76, 41.58, 34.60, 33.26, 25.63, 20.57, 20.01.

Example 23

4a'-methyl-(4'H,5'H,7'H)-spiro[1,3-dithiolane-2,2'-naphthalen]-5'(6'H)-one (239)

To a solution of Wieland-Miescher ketone (5.87 g, 33.0 mmol) in glacial acetic acid (40 mL) was added p-toluenesulfonic acid (2.94 g) followed by dropwise addition of 1,2-ethanedithiol over a 1 hour period. The reaction mixture was stirred at room temperature for another 4 hours, poured into 30 mL water, and stirred for 15 minutes. The white solid was filtered off, washed successively with water, diluted with NaHCO$_3$ solution and water, and then dried to yield thioketal 239 (7.33 g, 87.3%) as a white solid. $^1$H NMR (CDCl$_3$) δ 1.50-2.70 (m, 10H), 3.20-3.40 (m, 4H), 5.67 (s, 1H); $^{13}$C NMR (CDCl$_3$) 212.92, 141.23, 128.04, 64.81, 49.43, 40.11, 39.62, 37.92, 37.57, 30.81, 30.69, 24.73, 24.57.

Example 24

4a'-methyl-(4'H,5'H,7'H)-spiro[1,3-dithiolane-2,2'-naphthalen]-5'-carboxaldehyde (241)

To a cold (−30° C.) solution of (methoxymethyl)triphenylphosphonium chloride (6.753 g, 19.7 mmol) in THF (40 mL), was added KHMDS (0.5M in toluene, 35.46 mL, 17.73 mmol). The resulting red solution was stirred at 0° C. for 15 minutes before being treated with a solution of 241 (1 g, 3.94 mmol) in THF (10 mL). The mixture was stirred at room temperature for 24 hours. A solution of methanol in THF (1:1, 12 mL) and 4 N HCl (13 mL) was added to the reaction mixture at 0° C. The resulting solution was allowed to stir at room temperature for 36 hours, poured into water (40 mL) and extracted with ether (4×30 mL). The combined organic layers were washed with brine, dried (MgSO$_4$) and concentrated. Purification of the residue by flash chromatography on silica gel (1-3% ethyl acetate-hexanes) gave 783 mg (74%) of 241. $^1$H NMR (CDCl$_3$) δ 1.14 (s, 3H), 1.25-2.4 (m, 1H), 3.20-3.45 (m, 4H), 5.52 (s, 1H), 9.81 (d, J=2.0 Hz, 1H); $^{13}$C NMR (CDCl$_3$) 200.71, 139.59, 122.18, 61.37, 56.86, 36.40, 35.88, 33.56, 33.46, 33.06, 27.99, 22.15, 18.36, 15.84.

Example 25

{4a'-methyl-(4'H,5'H,7H)-spiro[1,3-dithiolane-2,2'-naphthalen]-5'yl}-(3,4,5-trimethoxy-phenyl)-methanol (243)

A solution 5-bromo-1,2,3-trimethoxy-benzene (276 mg, 1.12 mmol) dissolved in 6 mL anhydrous ether is cooled to −78° C. and tert-butyllithium (1.7 M in pentane, 1.32 mL, 2.24 mmol) is added. The mixture was stirred at −78° C. for 15 minute, then at room temperature for 3 hours. Aldehyde 241 (100 mg, 0.373 mmol) was added dropwise over 10 minutes in 10 mL ether at −30° C. The mixture was stirred for 0.5 hours and the reaction quenched with dropwise addition of saturated aqueous $NH_4^+Cl^-$. The phases were separated and the aqueous phase was extracted with ether (4×10 mL). The pooled organic extracts were washed with saturated aqueous $NaHCO_3$, brine, dried ($MgSO_4$), filtered and concentrated under vacuum. The residue was purified by flash chromatography over silica gel (25% ethyl acetate-hexanes) to yield 243 (119 mg, 73%).

Example 26

{4a'-methyl-(4'H,5H,7H)-spiro[1,3-dithiolane-2,2'-naphthalen]-5'yl}-(3-triisopropylhydroxyphenyl)-methanol (245)

Following the procedure of Example 25 but substituting 3-bromo-phenoxy)-triisopropyl-silane for 5-bromo-1,2,3-trimethoxy-benzene provided the triisopropyl derivative of {4a'-methyl-(4'H,5'H,7'H)-spiro[1,3-dithiolane-2,2'-naphthalen]-5'yl}-(3-triisopropylhydroxyphenyl)-methanol 245.

Example 27

(3a,7a-Dihydro-benzo[b]thiophen-3-yl)-{4a'-methyl-(4'H,5'H,7'H)-spiro[1,3-dithiolane-2,2'-naphthalen]-5'yl}-methanol (249)

Following the procedure of Example 26 but substituting 3-bromo-benzo[b]thiophene for 5-bromo-1,2,3-trimethoxy-benzene provided 249 in 54% yield.

Example 28

{4a'-methyl-(4'H,5'H,7'H)-spiro[1,3-dithiolane-2,2'-naphthalen]-5'yl}-phenyl-methanol (247)

Aldehyde 241 (200 mg, 0.746 mmol) was dissolved in 10 mL THF and cooled to −78° C. Phenylmagnesium bromide (1M in THF, 1.12 mL, 1.12 mmol) was added to the solution dropwise and the mixture was allowed to warm to room temperature over 2 hours. The reaction mixture was then cooled to 0° C. and quenched with 10 mL of water. The layers were separated and the aqueous layer was extracted with (3×10 mL) ether. The pooled organic extracts was washed with brine, dried ($MgSO_4$), filtered, and concentrated under vacuum. Purification by flash chromatography over silica gel (10% ethyl acetate-hexanes) afforded alcohol 247 (240 mg, 93%) as a white solid.

Example 29

5-(Hydroxy-phenyl-methyl)-4a-methyl 4,4a,5,6,7,8-hexahydro-3H-naphthalen-2-one (251)

Thioketal 245 (100 mg, 0.288 mmol) was dissolved in 3 mL $CHCl_3$ and 1 mL MeOH. A solution of $Hg(ClO_4)_2$ (253 mg, 0.633 mmol) in 3 mL MeOH was added dropwise. After 5 minutes of stirring at room temperature, the mixture was filtered and the filtrate was neutralized with 5 mL saturated $NaHCO_3$ solution. The layers were separated and the organic layer was extracted with $CHCl_3$ (3×5 ml). The pooled organic extracts were dried ($MgSO_4$) and filtered over a pad of alumina and celite. The filtrate was washed with $CH_2Cl_2$ and the solvents evaporated under vacuum to yield 251 (78 mg, 73%) as a white solid. $^1$H NMR ($CDCl_3$) δ 1.42 (s, 3H), 1.50-2.60 (m, 11H), 5.13 (d, J=4.0 Hz, 1H), 5.70 (s, 1H), 7.20-7.40 (m, 5H); $^{13}$C NMR ($CDCl_3$); HR-MS calculated for $C_{18}H_{22}O_2$: 270.1619, found: 270.1621.

Example 30

5-[Hydroxy-(3,4,5-trimethoxy-phenyl)-methyl]-4a-methyl-4,4a,5,6,7,8-hexahydro-3H-naphthalen-2-one (253)

Following the procedure of Example 29 but substituting thioketal 243 for thioketal 245 provided ketone 253 in 87% yield. $^1$H NMR ($CDCl_3$) δ 1.43 (s, 3H), 1.50-2.70 (m, 11H), 3.83 (s, 3H), 3.86 (s, 6H), 5.07 (s, 1H), 5.73 (s, 1H), 6.50 (s, 2H); $^{13}$C NMR ($CDCl_3$) 195.66, 167.64, 149.51, 149.36, 137.56, 132.95, 120.19, 99.99, 98.56, 67.52, 57.09, 52.40, 52.27, 35.89, 32.56, 30.15, 29.76, 22.42, 15.67, 15.03; HR-MS calculated for $C_{21}H_{28}O_5$: 360.1936, found: 360.1935.

Example 31

5-[(3a,7a-Dihydro-benzo[b]thiophen-3-yl)-hydroxy-methyl]-4a-methyl-4,4a,5,6,7,8-hexahydro-3H-naphthalen-2-one (255)

Following the procedure of Example 29 but substituting thioketal 249 for thioketal 245 provided ketone 255 in 87% yield. $^1$H NMR ($CDCl_3$) δ 1.43 (s, 3H), 1.70-2.00 (m, 6H), 2.15 (d, J=5.6 Hz, 1H), 2.20-2.65 (m, 7H), 5.41 (d, J=5.2 Hz, 1H), 5.76 (s, 1H), 7.18 (s, 1H), 7.27-7.40 (m, 2H), 7.76 (d, J=7.6 Hz, 1H), 7.91 (d, J=8.0 Hz, 1H); $^{13}$C NMR ($CDCl_3$); HR-MS calculated for $C_{20}H_{22}O_2S$: 326.1341, found: 326.1348.

Example 32

5-[Hydroxy-(3-hydroxy-phenyl)-methyl]4a-methyl-4,4a,5,6,7,8-hexahydro-3H-naphthalen-2-one: 84% (257)

Following the procedure of Example 29 but substituting thioketal 247 for thioketal 245 and then following the procedure of Example 13 gave 257 (53.8 mg, 84%) as a white solid. $^1$H NMR ($CDCl_3$) δ 1.36 (s, 3H), 1.40-2.80 (m, 12H), 5.01 (d, J=2.0 Hz, 1H), 5.70 (s, 1H), 6.60-6.90 (m, 2H), 7.15 (t, J=8.0 Hz, 1H), 7.62 (s, 1H); $^{13}$C NMR ($CDCl_3$); HR-MS calculated for $C_{18}H_{22}O_3$: 286.1569, found: 286.1570.

Example 33

[1-(4-Fluoro-phenyl)-4a-methyl-4,4a,5,6,7,8-hexahydro-1H-benzo[f]indazol-5-yl]-phenanthren-9-yl-methanol (259)

Following the procedure of Example 11 but substituting 9-bromophenanthrene for 3-bromo-benzo[b]thiophene gave (259) in 32% yield. $^1$H NMR ($CDCl_3$) δ 1.41 (s, 3H) 1.80 (m, 4H) 1.95 (d, J=11.72 Hz, 1H) 2.27 (m, 1H) 2.42 (m, 1H) 3.13 (d, J=14.65 Hz, 1H) 3.45 (d, J=14.65 Hz, 1H) 6.03 (d, J=2.93 Hz, 1H) 6.12 (d, J=1.95 Hz, 1H) 7.15 (t, J=8.79 Hz, 2H) 7.47 (dd, J=9.03, 4.64 Hz, 2H) 7.59 (s, 1H) 7.65 (m, 4H) 7.94 (d, J=7.32 Hz, 1H) 8.02 (s, 1H) 8.08 (d, J=7.81 Hz, 1H) 8.68 (d, J=7.81 Hz, 1H) 8.78 (d, J=6.84 Hz, 1H); $^{13}$C NMR ($CDCl_3$) 20.31, 20.38, 25.66, 33.32, 34.75, 42.62, 52.26, 69.15, 108.97, 113.82, 115.92, 116.14, 122.41, 123.27, 123.56, 125.01, 125.26, 125.34, 126.24, 126.61, 126.64, 126.84, 128.79, 129.24, 129.85, 130.74, 131.12, 135.84, 136.94, 137.97, 138.1, 151.08, 160.19.

Example 34

4a-Methyl-1-(3-phenylethynyl-phenyl)-1,4,4a,6,7,8-hexahydro-benzo[f]indazol-5-one (261)

Following the procedure of Example 3 but substituting (3-Phenylethynyl-phenyl)-hydrazine hydrochloride for 4-fluorophenylhydrazine hydrochloride gave (261) in 26% yield over two steps. $^1$H NMR (CDCl$_3$) δ 1.25 (s, 3H) 1.68 (m, 1H) 2.08 (m, 1H) 2.61 (m, 4H) 2.90 (d, J=2.93 Hz, 2H) 6.38 (d, J=1.47 Hz, 1H) 7.35 (m, 3H) 7.46 (m, 2H) 7.49 (s, 1H) 7.51 (s, 1H) 7.54 (dd, J=6.59, 3.17 Hz, 2H) 7.66 (s, 1H); $^{13}$C NMR (CDCl$_3$) 22.6, 23.2, 28.2, 31.5, 38.5, 50.6, 88.3, 90.3, 110.9, 114.3, 122.7, 123.2, 124.4, 126.2, 128.3, 128.5, 129.2, 130.1, 131.5, 135.8, 138.6, 139.6, 145.7, 212.5.

Compound 261 gave an IC50 of 174.4 nM in a GR binding assay.

Example 35

3-(4-fluoro-phenyl)-8-bromo-11b-methyl-5,6,12-trihydro-indazolo[5,6-a]carbazole (263)

Following the procedure of Example 3 but substituting 4-bromo-phenylhydrazine hydrochloride for 4-fluorophenylhydrazine hydrochloride gave 263 in 24% yield. $^1$H NMR (CDCl$_3$) δ 1.37 (s, 3H) 2.65 (m, 3H) 2.79 (d, J=15.63 Hz, 1H) 2.94 (dd, J=13.18, 3.91 Hz, 1H) 3.00 (d, J=15.14 Hz, 1H) 6.40 (s, 1H) 7.14 (d, J=3.42 Hz, 1H) 7.17 (d, J=3.42 Hz, 1H) 7.22 (m, 1H) 7.36 (s, 1H) 7.49 (m, 3H) 7.61 (d, J=1.95 Hz, 1H) 8.28 (s, 1H); $^{13}$C NMR (CDCl$_3$) 21.7, 24.7, 31.1, 33.4, 37.7, 108.8, 110.7, 112.1, 112.5, 114.4, 116.1, 116.3, 121.0, 124.2, 125.4, 125.4, 128.3, 128.6, 134.9, 135.5, 137.1, 137.9, 141.6, 147.5.

Example 36

3-(4-fluoro-phenyl)-8-methoxy-11b-methyl-5,6,12-trihydro-indazolo[5,6-a]carbazole (265)

Following the procedure of Example 3 but substituting 4-methoxy-phenylhydrazine hydrochloride for 4-fluorophenylhydrazine hydrochloride gave (265) in 16.8% yield. $^1$H NMR (CDCl$_3$) δ 1.39 (s, 3H) 2.69 (m, 3H) 2.82 (d, J=15.14 Hz, 1H) 2.99 (m, 2H) 3.86 (s, 3H) 6.41 (s, 1H) 6.83 (dd, J=8.79, 2.44 Hz, 1H) 6.96 (d, J=2.44 Hz, 1H) 7.18 (m, 2H) 7.22 (d, J=8.79 Hz, 1H) 7.51 (m, 3H) 7.88 (s, 1H); $^{13}$C NMR (CDCl$_3$) 22.0, 24.8, 31.3, 33.6, 37.7, 56.0, 100.8, 109.1, 110.6, 111.4, 114.6, 116.0, 116.2, 125.3, 125.3, 127.2, 128.3, 131.3, 135.7, 135.8, 137.1, 138.0, 141.2, 147.9, 154.1, 160.3, 162.8.

Example 37

3-(4-fluoro-phenyl)-8-fluoro-11b-methyl-5,6,12-trihydro-indazolo[5,6-a]carbazole (267)

In a 50 mL round bottom flask fitted with a Dean-Stark trap and condenser, a mixture of ketone (205) (150 mg, 0.51 mmol), 4-fluorophenylhydrazine hydrochloride (91 mg, 0.56 mmol), and sodium acetate (46 mg, 0.56 mmol), were dissolved in 10 mL glacial acetic acid and heated to 100° C. for 3 h. After cooling to room temperature, solvents were evaporated and the residue was purified by flash chromatography (30% EtOAc/benzene) to yield (269) (67.8 mg, 34%). $^1$H NMR (CDCl$_3$) δ 1.40 (s, 3H) 2.67 (m, 3H) 2.84 (d, J=15.14 Hz, 1H) 2.95 (t, J=4.88 Hz, 1H) 3.03 (d, J=15.14 Hz, 1H) 6.42 (s, 1H) 6.91 (td, J=9.16, 2.69 Hz, 1H) 7.13 (dd, J=9.77, 2.44 Hz, 1H) 7.19 (t, J=8.30 Hz, 2H) 7.24 (dd, J=8.79, 4.39 Hz, 1H) 7.50 (t, J=4.39 Hz, 2H) 7.59 (s, 1 H) 7.93 (s, 1H); $^{13}$C NMR (CDCl$_3$) 21.9, 24.8, 31.2, 33.6, 37.7, 103.4, 103.6, 109.5, 109.5, 109.8, 110.8, 111.2, 111.3, 114.4, 116.0, 116.3, 125.3, 125.4, 127.2, 127.3, 132.6, 137.0, 138.0, 142.2, 147.4, 156.7, 159.1, 160.3, 162.8.

Example 38

6-Anthracen-9-ylmethylene-1-(4-fluoro-phenyl)-4a-methyl-1,4,4a,6,7,8-hexahydro-benzo[f]indazol-5-one (269)

In a 100 mL round bottom flask, aldehyde (207) (100 mg, 0.337 mmol) and anthracene-9-carboxaldehyde (349 mg, 1.69 mmol) were dissolved in 10 mL THF and cooled to 0° C. Lithium hexamethyldisilylamide (LHMS) (370 µL, 0.370 mmol) was added dropwise, and the solution was stirred at room temperature for 16 hours. The reaction was quenched with 5 mL of saturated aqueous ammonium chloride. The aqueous layer was extracted with ether (3×10 mL), and the pooled organic extracts were washed with brine (10 mL), dried (MgSO$_4$) and then concentrated. Flash chromatography of the residue (0-25% EtOAc/hexanes) gave (269) (127.9 mg, 78%). $^1$H NMR (CDCl$_3$) δ 1.45 (s, 3H) 2.19 (m, 1H) 2.35 (m, 2H) 2.47 (m, 1H) 3.04 (d, J=16.11 Hz, 1H) 3.15 (d, J=16.11 Hz, 1H) 6.25 (s, 1H) 7.13 (t, J=8.55 Hz, 2H) 7.47 (m, 6H) 7.55 (s, 1H) 7.87 (m, 1H) 8.00 (m, 3H) 8.39 (s, 1H) 8.43 (s, 1H); $^{13}$C NMR (CDCl$_3$) 23.5, 27.2, 29.7, 30.2, 49.4, 110.4, 114.0, 115.9, 116.1, 125.0, 125.1, 125.2, 125.3, 125.5, 126.1, 127.5, 128.8, 128.9, 128.9, 129.0, 129.7, 131.1, 131.1, 135.5, 135.7, 135.7, 136.4, 138.5, 139.1, 145.2, 160.2, 162.6, 202.8.

Example 39

Binding Data for Compounds 263, 265, 267 and 269

Representative results of glucocorticoid receptor (GR) binding data for the compounds of Examples 35-38 are shown in Table 2, compared to dexamethasone.

TABLE 2

| Compound | GR Binding (IC50, nM) | GRE Activation GR | | Repression Coll A | |
| --- | --- | --- | --- | --- | --- |
| | | pot (EC50, nM) | Max fold activation | pot (EC50, nM) | % max repression |
| 263 | 708 | ND | ND | ND | ND |
| 265 | 239 | ND | ND | ND | ND |
| 267 | 130 | — | 18 | 100 | 75% |
| 269 | 43 | >5000 | — | >5000 | — |
| Dexamethasone | 25 | 3.7 | 50 | 0.36 | 84% |

Example 40

Binding Data for Compounds 221, 223, 227, 229, 231, 235, 237, 238, and 259

Representative results of glucocorticoid receptor (GR) binding data for the compounds of Examples 11-13, 18-22, and 33, are shown in Tables 3-5, compared to dexamethasone and other compounds.

TABLE 3

| Example | Compound | GR binding RBA (dex = 100) |
|---|---|---|
| 11 | 221 | 93 |
| 12 | 223 | 47 |
| 13 | 227 | 103 |
| 21 | 237 | 110 |
| 20 | 235 | 110 |
| 22 | 238 | 14, 39 |
| 18 | 229 | 52 |
| 19 | 231 | 36 |
| 33 | 259 | 72 |
| Dexamethasone | | 100 |

TABLE 4

| Example | Compound | GR pot (EC50, nM) | GRE activation max fold activation | PR max fold activation | MR max fold activation | AR max fold activation |
|---|---|---|---|---|---|---|
| 11 | 221 | 313 | 21 | — | 2.0 ± 0.7 | — |
| 11 | 221 | | | ND | ND | ND |
| 12 | 223 | 143 ± 27 | 32 ± 2 | — | — | — |
| 13 | 227 | 130 ± 43 | 95 ± 23 | 144 ± 32 | 3.2 ± 0.9 | 4.6 ± 1.6 |
| 21 | 237 | 149 ± 91 | 92 ± 18 | — | 5.0 ± 1.5 | — |
| 20 | 235 | 81 | 76 | — | — | — |
| 22 | 238 | 251 ± 118 | 86 ± 4 | 155 ± 32 | 6.2 ± 0.9 | — |
| 22 | 238 | 230 ± 80 | 112 ± 75 | 109 ± 10 | ND | — |
| 18 | 229 | 110 ± 7 | 55 ± 2 | — | 3.1 ± 1.0 | — |
| 19 | 231 | 330 ± 92 | 69 ± 25 | — | 2.9 ± 0.5 | — |
| 33 | 259 | >5000 | — | ND | ND | ND |
| Cortisol | | 78 ± 43 | 84 ± 2 | 53 ± 10 | 25 ± 5 | 15 ± 5 |
| Dexamethasone | | 2.2 ± 0.01 | 38 ± 16 | ND | 30 ± 2 | 23 ± 2 |
| Aldosterone | | 765 | 41 | ND | 6.1 ± 1.5 | — |
| Progesterone | | | | 255 ± 72 | ND | ND |
| Dihydrotestosterone (DHT) | | | | ND | ND | 46 ± 7 |

Example 41

Glucocorticoid Receptor Binding Assay. Tissue Culture, Transfection, and Luciferase Assays The Glucocorticoid Receptor Competitor Assay Kit (Panvera Corp, Madison, Wis.) was used for ligand binding studies. The recommended room temperature protocol was followed for all assayed ligands.

Plasmids for GR (human, pSG5 backbone), AP1-Luc (synthetic AP1 response element upstream of a firefly luciferase gene), $TAT_3$-Luc (three copies of the tyrosine aminotransferase glucocorticoid response element upstream of a firefly luciferase gene), β-galactosidase (used as a transfection control), as well as two stable transfected cells lines: an A549

TABLE 5

| | | AP-1 | | Repression Coll A | | NF-KB | |
|---|---|---|---|---|---|---|---|
| Example | Compound | pot (EC50, nM) | % max repression | pot (EC50, nM) | % max repression | pot (EC50, nM) | % max repression |
| 11 | 221 | 5.3 | 74% | | | | |
| 11 | 221 | ND | ND | | | | |
| 12 | 223 | 6.7 | 74% | | | | |
| 13 | 227 | 6 | 77% | 6.9 | 75% | | |
| 21 | 237 | 4.9 | 80% | 8.1 | 75% | 26.4 | 74% |
| 20 | 235 | 16.6 | 74% | | | | |
| 22 | 238 | 19.1 | 75% | 27 | 68% | | |
| 22 | 238 | 14.7 | 73% | | | | |
| 18 | 229 | 16.6 | 77% | | | | |
| 19 | 231 | 12.8 | 68% | 28 | 70% | | |
| 33 | 259 | ND | ND | 783 | 73% | | |
| Cortisol | | 0.78 | 90% | 2.1 | | 8.4 | 83% |
| Dexamethasone | | 0.15 | 89% | 0.36 | 84% | 1.5 | 87% |

(human, lung carcinoma) cell line stably transfected with a κB response element upstream of a firefly luciferase gene, (R. M. Nissen et al., *Genes Dev.,* 14(18):2314-29, (2000)) and a U2OS (human, osteosarcoma) stably transfected with rat GR (I. Rogatsky, et al., *Mol. Cell. Biol.,* 1997, 17, 3181-3193) were a gift of Professor Keith Yamamoto (Department of Biochemistry, University of California, San Francisco).

For $TAT_3$ activation assays, CV-1 cells were grown in 0.1 µm filtered DME supplemented with 4.5 g/L glucose, 0.584 g/L L-glutamine, 3.7 g/L $NaHCO_3$, 110 mg/L streptomycin sulfate, 100 units/ml of penicillin G and 5% fetal bovine serum. Cells were plated into tissue culture treated, 96 well flat bottom plates (25,000 cells/well), and incubated for 12 h at 37° C. Cells were then transfected using the Lipofectamine PLUS transfection reagent (Gibco BRL). DNA-lipid complexes of 5 ng GR, 50 ng $TAT_3$-Luc, 7.5 ng β-galactosidase, 1 µL-well PLUS reagent and 0.67 µL-well lipofectamine in 50 µL/well serum free media were added to cells and incubated for 4 h at 37° C. Complexes were removed and hormones diluted in 5% charcoal-stripped FBS were added to the cells, which were then incubated for 24 hours at 37° C. Media was removed and the cells were washed with 100 µL $Ca^{+2}$, $Mg^{+2}$ free phosphate buffered saline (PBS). Lysis was achieved by adding 50 µL of Passive Lysis Buffer (Promega Corp, Madison, Wis.) and shaking the plate for 15 min. 15 µL of this lysate was then used to assay β-galactosidase activity (β-galactosidase enzyme assay system, Promega Corp., recommended procedures followed). The Luciferase Assay System (Promega Corp.) was used to assay luciferase activity. 100 µL of luciferase assay reagent was added rapidly to the plate and luminescence was measured for 10 ms/well on an Analyst AD Detection System (LJL Biosystems, Sunnyvale, Calif.).

For AP1 repression assays, U2OS cells stably transfected with rat GR were grown in similar media as for CV-1 cells with the exception of the FBS concentration, which was 10% and the only antibiotic was 350 µg/mL. Cells were plated and transfected in a similar fashion, except for plasmids, which in this case were 50 ng/well AP1-Luc and 10 ng/well β-galactosidase. Post-transfection, cells were incubated with either 50 ng/mL TPA (Phorbol 12-myristate 13-acetate), or 50 ng/mL TPA and various hormone dilutions in 10% charcoal treated FBS media. The cells were incubated for 12 h, and the lysis, β-galactosidase assay, and luciferase assay were performed as previously described.

For NF-κB repression assays, A549 cells stably transfected with a luciferase reporter were grown under the same conditions as CV-1 cells. 50,000 cells/well were plated into 96 well plates and incubated for 12 h at 37° C. Either TNF-α alone or mixed with various hormone dilutions in media were then added to the cells, which were then incubated for 8 hours. Procedures for lysis and luciferase assay were performed as previously described. Protein content was used as a control in this case and the recommended procedures using the BCA Protein Assay Kit (Roche) were followed.

The compounds of the invention possessed significant binding affinity for the glucocorticoid receptor (greater than 1.0 µm). The transactivation data indicated that the compounds of the invention were able to selectively disassociate the different response elements of the glucocorticoid receptor.

Finally, it should be noted that there are alternative ways of implementing both the present invention. Accordingly, the present embodiments are to be considered as illustrative and not restrictive, and the invention is not to be limited to the details given herein, but may be modified within the scope and equivalents of the appended claims.

All patents and other publications cited herein are incorporated herein by reference in their entirety for all purposes.

What is claimed is:
1. A compound according to the structural formula:

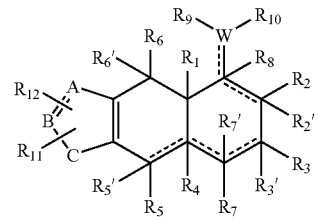

or a pharmaceutically available salt thereof, wherein:

A, B and C are independently carbon or nitrogen provided that one of A, B and C is nitrogen and that two of A, B and C are carbon;

W is carbon, oxygen, nitrogen, or sulfur and, when W is other than carbon and nitrogen, one or more of $R_8$, $R_9$ and $R_{10}$ is absent so that a normal valence on W is maintained;

$R_1$ is hydrogen, alkyl, substituted alkyl, acyl, substituted acyl, acylamino, substituted acylamino, amino, alkylamino, substituted alkylamino, dialkylamino, substituted dialkylamino, alkoxycarbonyl, substituted alkoxycarbonyl, arylalkyl, substituted arylalkyl, aryloxycarbonyl, substituted aryloxycarbonyl, carbamoyl, substituted carbamoyl, carboxy, cyano, halo, heteroalkyl or substituted heteroalkyl, heteroarylalkyl or substituted heteroarylalkyl;

$R_2$, $R_3$, $R_5$, $R_6$, $R_6'$ and $R_7$ are independently hydrogen, alkyl, substituted alkyl, acyl, substituted acyl, acylamino, substituted acylamino, alkoxy, substituted alkoxy, amino, alkylamino, substituted alkylamino, dialkylamino, substituted dialkylamino, alkylsulfonyl, substituted alkylsulfonyl, alkylsulfinyl, substituted alkylsulfinyl, alkylthio, substituted alkylthio, alkoxycarbonyl, substituted alkoxycarbonyl, arylalkyl, substituted arylalkyl, aryloxycarbonyl, substituted aryloxycarbonyl, carbamoyl, substituted carbamoyl, carboxy, cyano, halo, heteroalkyl, substituted heteroalkyl, heteroarylalkyl, substituted heteroarylalkyl or hydroxy;

$R_2'$, $R_3'$, $R_5'$, $R_7'$ and $R_8$ are absent or are independently hydrogen, alkyl, substituted alkyl, acyl, substituted acyl, acylamino, substituted acylamino, alkoxy, substituted alkoxy, amino, alkylamino, substituted alkylamino, dialkylamino, substituted dialkylamino, alkylsulfonyl, substituted alkylsulfonyl, alkylsulfinyl, substituted alkylsulfinyl, alkylthio, substituted alkylthio, alkoxycarbonyl, substituted alkoxycarbonyl, arylalkyl, substituted arylalkyl, aryloxycarbonyl, substituted aryloxycarbonyl, carbamoyl, substituted carbamoyl, carboxy, cyano, halo, heteroalkyl, substituted heteroalkyl, heteroarylalkyl, substituted heteroarylalkyl or hydroxy;

$R_4$ is absent or is hydrogen, alkyl, substituted alkyl, acyl, substituted acyl, acylamino, substituted acylamino, amino, alkylamino, substituted alkylamino, dialkylamino, substituted dialkylamino, alkoxycarbonyl, substituted alkoxycarbonyl, arylalkyl, substituted arylalkyl, aryloxycarbonyl, substituted aryloxycarbonyl, carbamoyl, substituted carbamoyl, carboxy, cyano, halo, heteroalkyl, substituted heteroalkyl, heteroarylalkyl or substituted heteroarylalkyl;

R$_9$ is hydrogen, alkyl, substituted alkyl, alkoxy, substituted alkoxy, amino, alkylamino, substituted alkylamino, dialkylamino, substituted dialkylamino, carboxy, cyano, halo, oxo, thio, hydroxy or is absent;

R$_{10}$ is hydrogen, alkyl, substituted alkyl, acyl, substituted acyl, alkoxycarbonyl, substituted alkoxycarbonyl, aryl, substituted aryl, arylalkyl, substituted arylalkyl, aryloxycarbonyl, substituted aryloxycarbonyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl, substituted heteroarylalkyl or is absent;

R$_{10}$ and R$_2$ may bond directly to one another to form a ring, and an additional ring, which may itself be substituted with an alkyl, alkoxy, halo, alkyl, substituted alkyl, acyl, substituted acyl, cycloalkyl, or substituted cycloalkyl, may fuse to the bond between R$_{10}$ and R$_2$;

R$_{11}$ and R$_{12}$ are independently hydrogen, alkyl, substituted alkyl, acyl, substituted acyl, acylamino, substituted acylamino, alkoxy, substituted alkoxy, amino, alkylamino, substituted alkylamino, dialkylamino, substituted dialkylamino, alkylsulfonyl, substituted alkylsulfonyl, alkylsulfinyl, substituted alkylsulfinyl, alkylthio, substituted alkylthio, alkoxycarbonyl, substituted alkoxycarbonyl, aryl, substituted aryl, arylalkyl, substituted arylalkyl, aryloxycarbonyl, substituted aryloxycarbonyl, carbamoyl, substituted carbamoyl, carboxy, cyano, halo, oxo, thio, heteroalkyl, substituted heteroalkyl, heteroaryl, substituted heteroaryl, heteroarylalkyl, substituted heteroarylalkyl or hydroxy; and one of the bonds in formula (I) that are shown with single and dashed lines is a double bond provided that normal valences of W and the atoms in the rings are satisfied.

2. The compound of claim 1, wherein R$_1$ and R$_4$ are independently hydrogen, alkyl, substituted alkyl, acyl, substituted acyl, alkoxycarbonyl, substituted alkoxycarbonyl, carboxy, cyano, carbamoyl, substituted carbamoyl, heteroalkyl and substituted heteroarylalkyl.

3. The compound of claim 1, wherein R$_1$ and R$_4$ are independently hydrogen, alkanyl or substituted alkanyl.

4. The compound of claim 1, wherein R$_2$, R$_3$, R$_5$, R$_6$, R$_6$', and R$_7$ are independently hydrogen, alkyl, substituted alkyl, acyl, substituted acyl, alkoxy, substituted alkoxy, amino, alkoxycarbonyl, substituted alkoxycarbonyl, carbamoyl, substituted carbamoyl, carboxy, cyano, halo, heteroalkyl, substituted heteroalkyl, or hydroxy.

5. The compound of claim 1, wherein R$_2$, R$_2$', R$_3$, R$_5$, R$_6$, R$_6$', R$_7$ and R$_8$ are independently hydrogen, alkanyl or substituted alkanyl.

6. The compound of claim 1, wherein R$_4$ and R$_5$' are absent.

7. The compound of claim 1, wherein R$_4$ and R$_7$' are absent.

8. The compound of claim 1, wherein R$_3$' and R$_7$' are absent.

9. The compound of claim 1, wherein R$_3$', R$_5$' and R$_7$' are independently hydrogen, alkyl, substituted alkyl, acyl, substituted acyl, alkoxy, substituted alkoxy, amino, alkoxycarbonyl, substituted alkoxycarbonyl, carbamoyl, substituted carbamoyl, carboxy, cyano, halo, heteroalkyl, substituted heteroalkyl, or hydroxy.

10. The compound of claim 1, wherein R$_3$', R$_5$' and R$_7$' are independently hydrogen, alkanyl or substituted alkanyl.

11. The compound of claim 1, wherein R$_9$ is hydrogen, alkoxy, substituted alkoxy, halo, oxo, thio, hydroxy or is absent.

12. The compound of claim 1, wherein R$_{10}$ is hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, substituted heteroarylalkyl or is absent.

13. The compound of claim 1, wherein R$_{11}$ and R$_{12}$ are independently hydrogen, alkyl, alkoxy, amino, alkylamino, dialkylamino, alkylsulfonyl, alkylsulfinyl, alkylthio, alkoxycarbonyl, substituted alkoxycarbonyl, aryl, substituted aryl, arylalkyl, substituted arylalkyl, carbamoyl, carboxy, cyano, halo, oxo, thio, heteroalkyl, heteroaryl, substituted heteroaryl, heteroarylalkyl, substituted heteroarylalkyl or hydroxy.

14. The compound of claim 1, wherein R$_{11}$ and R$_{12}$ are independently hydrogen, aryl, substituted aryl, arylalkyl, substituted arylalkyl, oxo, heteroalkyl, heteroaryl, substituted heteroaryl, heteroarylalkyl, substituted heteroarylalkyl or hydroxy.

15. The compound of claim 1, wherein R$_1$, R$_2$, R$_2$', R$_3$, R$_3$', R$_5$, R$_6$, R$_6$', R$_7$, R$_7$' and R$_8$ are hydrogen, alkyl or arylalkyl and R$_4$ and R$_5$' are absent.

16. The compound of claim 15, wherein R$_9$ is alkoxy, oxo or hydroxy.

17. The compound of claim 15, wherein R$_{10}$ is aryl, substituted aryl, heteroaryl or substituted heteroaryl.

18. The compound of claim 1, wherein R$_1$ is methyl, R$_2$, R$_2$', R$_3$, R$_3$', R$_5$, R$_6$, R$_6$', R$_7$, R$_7$' and R$_8$ are hydrogen, R$_4$ and R$_5$' are absent, R$_9$ is alkoxy, oxo or hydroxy, R$_{10}$ is aryl, substituted aryl, heteroaryl or substituted heteroaryl, C is nitrogen, A and B are carbon, R$_{11}$ is hydrogen and R$_{12}$ is aryl, substituted aryl, heteroaryl or substituted heteroaryl.

19. The compound of claim 1, wherein W is oxygen, and R$_8$, R$_9$ and R$_{10}$ are all absent.

20. The compound of claim 1, wherein R$_{10}$ and R$_2$ bond directly to one another to form a 5-membered ring, W is nitrogen, R$_9$ is hydrogen, R$_8$ and R$_2$' are both absent, and a benzene ring is fused to the bond between R$_{10}$ and R$_2$.

21. A method for selectively modulating the activation, repression, agonism or antagonism effects of the glucocorticoid receptor in a patient, comprising administering to said patient a therapeutically effective amount of a compound according to claim 1.

22. A compound according to claim 1, wherein the compound is an antagonist of the glucocorticoid receptor.

23. A compound according to claim 1, wherein the compound is an agonist of the glucocorticoid receptor.

24. A pharmaceutical composition comprising the compound of claim 1.

* * * * *